United States Patent
Endo et al.

(10) Patent No.: US 7,273,615 B2
(45) Date of Patent: Sep. 25, 2007

(54) REACTION SOLUTION FOR CELL-FREE PROTEIN SYNTHESIS, METHOD OF PREPARING THE SAME, AND PROTEIN SYNTHESIS METHOD USING THE SAME

(75) Inventors: Yaeta Endo, Matsuyama (JP); Takayasu Kawasaki, Matsuyama (JP); Tatsuya Sawasaki, Matsuyama (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 51 days.

(21) Appl. No.: 10/506,127

(22) PCT Filed: Feb. 28, 2003

(86) PCT No.: PCT/JP03/02313

§ 371 (c)(1),
(2), (4) Date: Nov. 4, 2004

(87) PCT Pub. No.: WO03/072796

PCT Pub. Date: Sep. 4, 2003

(65) Prior Publication Data

US 2005/0148046 A1    Jul. 7, 2005

(30) Foreign Application Priority Data

Feb. 28, 2002   (JP)   ............... 2002-053161

(51) Int. Cl.
*A61K 36/00*   (2006.01)
*A61K 38/00*   (2006.01)

(52) U.S. Cl. .............. 424/195.15; 424/278.1; 530/323

(58) Field of Classification Search ........... 530/350, 530/323; 435/70.1, 25, 189, 215; 514/2, 514/12; 424/195.15, 278.1
See application file for complete search history.

(56) References Cited

U.S. PATENT DOCUMENTS

| | | | |
|---|---|---|---|
| 6,548,276 B2 * | 4/2003 | Swartz et al. | 435/70.1 |
| 6,905,843 B1 * | 6/2005 | Endo et al. | 435/69.1 |
| 2003/0162245 A1 * | 8/2003 | Endo et al. | 435/68.1 |

FOREIGN PATENT DOCUMENTS

| | | |
|---|---|---|
| JP | 05-336986 A | 12/1993 |
| JP | 07-000194 A | 1/1995 |
| JP | 10-080295 A | 3/1998 |
| JP | 2003-116590 | 4/2003 |
| WO | WO 00/68412 | 11/2000 |

OTHER PUBLICATIONS

Mcginnes et al. (1996) Role of cotranslational disulfide bond formation in the folding of the hemagglutinin-neuraminidase protein of Newcastle disease virus. Virology. vol. 224, pp. 465-476.*

Schafer et al. (2001) Redox environment of the cell as viewed through the redox state of the glutathione disulfide/glutathione couple. Free Radic. Biol. Med. vol. 30, pp. 1191-1212.*

Gharakhanian et al. (19950 SV40 VP1 assembles into disulfide-linked postpentameric complexes in cell-free lysates. Virology. vol. 207, pp. 251-254.*

Yilla et al. (19920 Early disulfide bond formation prevents heterotypic aggregation of membrane proteins in a cell-free translation system. J. Cell. Biol. vol. 118, pp. 245-252.*

Merk et al. (1999) Cell-free expression of two single-chain monoclonal antibodies against lysozyme: effect of domain arrangement on the expression. J. Biochem. (Tokyo). vol. 125, pp. 328-333.*

Erickson et al. (1983) Cell-free translation of messenger RNA in a wheat germ system, Meth. Enzymol. vol. 96, pp. 38-50.*

Madin (2000) A highly efficient and robust cell-free protein synthesis system prepared from wheat embryos: plants apparently contain a suicide system directed at ribosomes. Proc. Natl. Acad. Sci. U S A. vol. 97, No. 2, pp. 559-564.*

Ogasawara et al. (1999) A new class of enzyme acting on damaged ribosomes: ribosomal RNA apurinic site specific lyase found in wheat germ. EMBO J. 1999, vol. 18, No. 22, 6522-6531.*

Jackson et al. (1983) Preparation and use of nuclease-treated rabbit reticulocyte lysates for the translation of eukaryotic messenger RNA. Methods Enzymol. vol. 96, pp. 50-74.*

Moldave et al. (1983) Preparation of a cell-free system from Chinese hamster ovary cells that translates natural and synthetic messenger ribonucleic acid templates. Methods Enzymol. vol. 101, pp. 629-635.*

Madin et al. (2000) A highly efficient and robust cell-free protein synthesis system prepared from wheat embryos: plants apparently contain a suicide system directed at ribosomes. Proc. Natl. Acad. Sci. U S A. vol. 97, No. 2, pp. 559-564.*

International Preliminary Examination Report for PCT/JP2003/002313.

International Search Report for PCT/JP03/02313, dated Jun. 10, 2003.

(Continued)

*Primary Examiner*—Kathleen Kerr Bragdon
*Assistant Examiner*—Samuel Wei Liu
(74) *Attorney, Agent, or Firm*—Kilyk & Bowersox, P.L.L.C.

(57) ABSTRACT

The present invention provides a cell-free protein synthesis method characterized by a cell-free protein synthesis reaction solution that is weakly reducing and suitable for protein folding, performing a weakly reducing synthesis reaction, and preferably performing a translation reaction with the further addition of a substance catalyzing a disulfide bond exchange reaction at the beginning of the translation reaction. This method allows for proper formation of intramolecular disulfide bonds in the protein and efficiently provides protein having substantially the same function as the original protein. Specifically, it provides antibody protein that binds specifically to an antigen.

3 Claims, 10 Drawing Sheets

OTHER PUBLICATIONS

Ryabova et al., "Functional antibody production using cell-free translation: Effects of protein disulfide isomerase and chaperones," *Nature Biotechnology*, vol. 15, No. 1, pp. 79-84 (1997).

John et al., "Cell-free synthesis and assembly of prolyl 4-hydroxylase: the role of the β-subunit (PDI) in preventing misfolding and aggregation of the α-subunit," *The EMBO Journal*, vol. 12, No. 4, pp. 1587-1595 (1993).

Jiang et al., "Expression of Fab Fragment of Catalytic Antibody 6D9 in an *Escherichia coli* in Vitro Coupled Transcription/Translation System," FEBS Letters, No. 514, pp. 290-294 (2002).

Iwasaki et al., "Importance of Disulfide Bridge Formation on Folding of Phospholipase D from *Streptomyces antibioticus*," Journal of Bioscience and Bioengineering, vol. 89, No. 5, pp. 506-508 (2000).

Jacob et al., "Folding of Human Intestinal Lactase-phlorizin Hydrolase," The Journal of Biological Chemistry, vol. 270, No. 31, pp. 18678-18684 (Aug. 4, 1995).

Yilla, et al. "Early disulfide bond formation prevents heterotypic aggregation of membrane proteins in a cell-free translation system," *The Journal of Cell Biology*, vol. 118, No. 2, pp. 245-252 (1992).

* cited by examiner

Solvent:
no.1-8: 50mMTris8.0
no. 9-13: 0.15MNaCl/50mMTris8.0
no. 14-22: 4%SDS/50mMTris8.0

SEQUENCE LISTING

<160> NUMBER OF SEQ ID NOS: 8

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
ctaccagatc tgccatgcag atcgttgtta cccagg                               36

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gcttgggccc agagctcacg gtcaggctcg                                      30

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ggctaagagc tcacggtcag gctcg                                           25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
gcctgcagct ggcgccatcg at                                              22

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
ctgcggcagc cgcttactgg ggtcagggtg                                      30

<210> SEQ ID NO 6
<211> LENGTH: 30
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 6
ccgctgcggc agccgtgcag tagtaaaccg                                          30

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tggggtcagg gtgcgagcct g                                                   21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gtaatcaccg tagtaatcat g                                                   21
```

REACTION SOLUTION FOR CELL-FREE PROTEIN SYNTHESIS, METHOD OF PREPARING THE SAME, AND PROTEIN SYNTHESIS METHOD USING THE SAME

This application is a National Stage Application of PCT/JP03/02313, filed Feb. 28, 2003, which claims priority from Japanese Patent Application No. JP 2002-53161, filed Feb. 28, 2002.

TECHNICAL FIELD

The present invention relates to a method for efficiently synthesizing a protein having at least one intramolecular disulfide bond in the protein, by way of cell-free protein synthesis, and to a protein prepared by way of this method.

BACKGROUND ART

The development of technologies allowing proteins to be synthesized at will are expected to contribute greatly, not only to the fields of the life sciences and biotechnology, but also to the design of nano-machines and the development of molecular components in such engineering fields as neural computing. Currently, genetic engineering techniques for introducing cloned DNA into living cells are widely used for protein synthesis, but exogenous proteins that can be produced by these methods are limited to molecules that are able to survive the life support mechanisms of their host. Meanwhile, advances in organic synthesis technology have made automatic synthesizers common, but while peptides comprising a few dozen amino acids are routinely synthesized, chemical synthesis of higher molecular weight proteins is currently extremely difficult, due to limitations in terms of the yield, side reactions, and the like. Furthermore, there has been strong ethical criticism in Europe and the United States of conventional using living organisms to produce proteins, or to search for novel molecules, and there is a concern that international regulations will become even stricter.

Cell-free protein synthesis is an example of a novel protein synthesis method capable of overcoming these problems, which applies biochemical procedures and attempts to make maximal use of the outstanding characteristics of living organisms. These methods provide biological systems for the translation of genetic information within artificial containers and, using nucleic acids which have been designed and synthesized as templates, reconstruct systems capable of incorporating the desired amino acids, including those which do not exist in nature. As these systems are not subject to the limitations of living organisms, it can be expected that an almost limitless range of protein molecules can be synthesized.

With regard to cell-free protein synthesis systems, it was reported 40 years ago that pulped cell sap retained the ability to synthesize protein, and various methods of doing this have been developed in the past. Currently, cell extracts derived from *E. coli*, wheat embryo and rabbit reticulocytes are widely employed in protein synthesis and the like.

The inventors have already shown, based on the findings of past research into ribosome inactivating toxins, that the extreme drop in protein synthesis activity seen in cell-free protein synthesis systems using wheat embryo extract were the result of a switch for an auto ribosome inactivation mechanism (cell suicide mechanism), which is programmed into the original cell as a defense mechanism against pathogenic microorganisms, and which is triggered by grinding the embryo (Madin, K. et al., *Proc. Nat'l. Acad. Sci.* USA, 97, 559-564 (2000)). Then, it was demonstrated that protein synthesis reactions using wheat embryo extract that was prepared by a novel method, wherein tritin activity and the like were eliminated from embryo tissues, exhibited good protein synthesis characteristics over a long period of time (Madin, K. et al., *Proc. Nat'l. Acad. Sci.* USA, 97, 559-564 (2000), JP-2000-236896-A).

However, in general, in the preparation of cell extracts for cell-free protein synthesis and performing translation reactions in the cell-free protein synthesis systems, as highly reducing conditions are required, proteins having at least one intramolecular disulfide bond cannot be formed. Consequently, there was a problem in that proteins having at least one intramolecular disulfide bond, which were prepared by conventional cell-free protein synthesis systems, often did not take on a three-dimensional structure and did not, therefore, have the original functions of the protein.

DISCLOSURE OF THE INVENTION

An object of the present invention is to provide a method for efficiently synthesizing proteins in which intramolecular disulfide bonds are properly formed (retained) in cell-free protein synthesis reactions, and to provide a protein prepared by this method having substantially the same function as the original function of the protein.

As a result of earnest study on the part of the present inventors, directed at solving the problem described above, it was discovered that, if a solution for a transcription reaction was prepared by gel filtration of wheat embryo extract using a Sephadex G-25 column, which was equilibrated with buffer solution that did not contain dithiothreitol, and protein disulfide isomerase was further added thereto, when a single chain antisalmonella antibody was synthesized, the resulting antibody bound specifically to an antigen. The present invention was accomplished based on these observations.

That is to say, the present invention is as described hereinafter.

(1) A cell-free protein synthesis reaction solution having a redox potential sufficient to allow formation of at least one disulfide bond in a protein molecule.

(2) The cell-free protein synthesis reaction solution set forth above in (1), wherein the redox potential is −100 mV to 0 mV.

(3) The cell-free protein synthesis reaction solution set forth above in (1) or (2), comprising at least one reducing agent selected from dithiothreitol, 2-mercaptoethanol and glutathione/oxidized glutathione.

(4) A cell-free protein synthesis reaction solution comprising 20 µM to 70 µM of dithiothreitol.

(5) A cell-free protein synthesis reaction solution comprising 0.1 mM to 0.2 mM of 2-mercaptoethanol.

(6) A cell-free protein synthesis reaction solution comprising 30 µM to 50 µM/1 µM to 5 µM of glutathione/oxidized glutathione.

(7) The cell-free protein synthesis reaction solution set forth above in any one of (1) to (6), comprising a substance catalyzing a disulfide bond exchange reaction.

(8) The cell-free protein synthesis reaction solution set forth above in (7), wherein the substance catalyzing the disulfide bond exchange reaction is protein disulfide isomerase.

(9) A method for preparing a cell-free protein synthesis reaction solution comprising a step of adjusting the redox potential of a cell extract for cell-free protein synthesis to a redox potential sufficient to allow formation of at least one disulfide bond in a protein molecule.

(10) The method for preparation set forth above in (9), characterized by passing the cell extract for cell-free protein synthesis that contains the reducing agent through a gel filtration carrier, which has been pre-equilibrated with a buffer solution that does not contain the reducing agent.

(11) A method for selecting a concentration range for a reducing agent in a cell-free protein synthesis reaction solution comprising:
(1) performing a translation reaction with a plurality of cell-free protein synthesis reaction solutions each comprising a mutually different concentration of a reducing agent, followed by measuring the solubilization rate of the synthesized proteins in the reaction solutions;
(2) performing translation reactions with a plurality of cell-free protein synthesis reaction solutions, which are the same as described above in (1), other than the fact that a substance catalyzing a disulfide bond exchange reaction has been added, followed by measuring the solubilization rate of the synthesized proteins in the reaction solutions;
(3) comparing the solubilization rates measured above in (1) and (2); and
(4) selecting the concentration range for the reducing agent at which the solubilization rate is increased by the presence of the substance catalyzing the disulfide bond exchange reaction and the concentration range showing, absence of the substance, a solubilization rate greater than or equal to the solubilization range for the aforementioned concentration range in the presence of the substance.

(12) The method set forth above in (11), characterized by measuring the amounts of protein synthesized in each of the cell-free protein synthesis reaction solutions comprising the reducing agent in the selected concentration ranges, and selecting the reducing agent concentration range at which the greatest amount of protein is synthesized.

(13) The method set forth above in (11) or (12), wherein the reducing agent is selected from at least one of dithiothreitol, 2-mercaptoethanol and glutathione/oxidized glutathione.

(14) A protein synthesis method characterized in that, in a cell-free protein synthesis system, a translation reaction is performed using a cell-free protein synthesis reaction solution comprising a reducing agent in a concentration range selected according to the method set forth above in (11) to (13).

(15) A protein synthesis method characterized in that, in a cell-free protein synthesis system, a translation reaction is performed using a cell-free protein synthesis reaction solution comprising 20 µM to 70 µM of dithiothreitol.

(16) A protein synthesis method characterized in that, in a cell-free protein synthesis system, a translation reaction is performed using a cell-free protein synthesis reaction solution comprising 0.1 mM to 0.2 mM of 2-mercaptoethanol.

(17) A protein synthesis method characterized in that, in a cell-free protein synthesis system, a translation reaction is performed using a cell-free protein synthesis reaction solution comprising 30 µM to 50 µM/1 µM to 5 µM of glutathione/oxidized glutathione.

(18) The method set forth above in (14) to (17) wherein a substance catalyzing a disulfide bond exchange reaction has been added to the cell-free protein synthesis reaction solution used.

(19) The method set forth above in (18) wherein the substance catalyzing the disulfide bond exchange reaction is added to the cell-free protein synthesis reaction solution at the beginning of the translation reaction.

(20) The method set forth above in (18) or (19), wherein the substance catalyzing the disulfide bond exchange reaction is protein disulfide isomerase.

(21) A protein obtained by use of the method set forth above in (14) to (20).

(22) A protein synthesized using a cell-free protein synthesis system, characterized by retaining at least one intramolecular disulfide bond.

(23) The protein set forth above in (22), characterized by having substantially the same function as the original protein.

(24) The protein set forth above in (22) or (23), which is an antibody protein, a secretory protein or a membrane protein.

Figure 1:
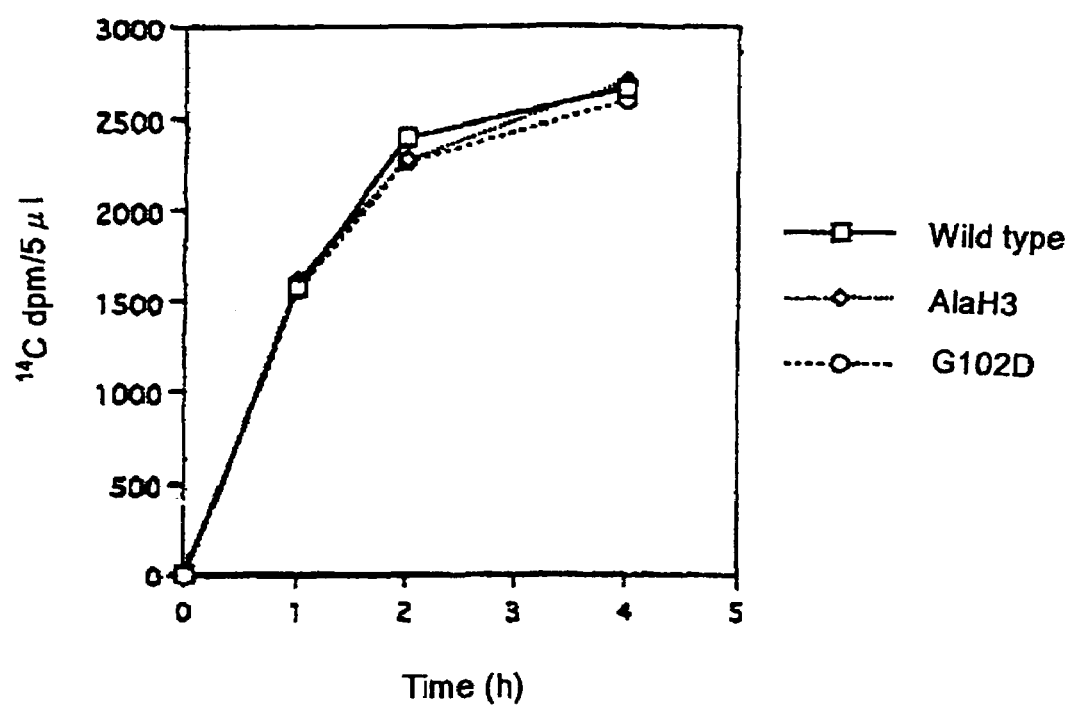
FIG. 1 is a graph showing the amount of protein synthesized by a weakly reducing synthesis reaction solution.

DETAILED DESCRIPTION OF THE INVENTION (1) Cell-Free Protein Synthesis Reaction Solution Capable of Forming Disulfide Bonds The present invention relates to a method whereby protein can be synthesized in a cell-free protein synthesis system in such a way that intramolecular disulfide bonds are properly formed (retained). The present invention also relates to a cell-free protein synthesis reaction solution for the same.

A cell-free protein synthesis systems are methods performed in vitro, wherein components including ribosomes and the like, which are intracellular protein translation apparatus, are extracted from an organism, and to this extract (hereinafter referred to as "cell extract for cell-free protein synthesis") are added a template (transcription template or translation template), nucleic acids and amino acids, which serve as substrates, an energy source, and if necessary various ions, a buffering solution, and other additives that are desirable for transcription or translation reactions. These include methods wherein a translation reaction is performed using mRNA as a translation template (hereinafter also referred to as "cell-free translation systems") and those wherein DNA is used as a transcription template, and a transcription reaction is performed by adding factors necessary for transcription, such as RNA polymerase, whereafter a translation reaction is performed with the product of the transcription reaction (mRNA) as the translation template (hereinafter also referred to as "cell-free transcription/translation systems"). The cell-free protein synthesis system of the present invention includes both the aforementioned cell-free translation systems and the aforementioned cell-free transcription/translation systems.

In order to synthesize a protein in which intracellular disulfide bonds are properly formed (retained), the present invention is characterized by performing the translation reaction under less strongly reducing conditions than was conventional. Herein, the expression "the translation reaction is performed under less strongly reducing conditions than was conventional" refers to performing a translation reaction using a cell-free protein synthesis reaction solution wherein the redox potential is −100 mV to 0 mV (preferably −50 mV to −5 mV) {the redox potential of conventional commonly used cell-free protein synthesis reaction solutions being −300 mV to −150 mV} (hereinafter the cell-free protein synthesis reaction solution of the present invention may also be referred to as a "weakly reducing synthesis reaction solution"). Note that the redox potential of the cell-free protein synthesis reaction solution can be measured using the oxidation reduction potential (ORP) controller FO-2000 (EYELA) according to the operation manual. This may, for example, be measured by preparing approximately 3 ml of synthesis reaction solution, incubating at 26° C., immersing electrodes used for measurement of the electric potential in the solution, then waiting for the measured value to stabilize (approximately 15 to 30 minutes) and recording the stabilized value.

The weakly reducing synthesis reaction solution of the present invention having a redox potential within the range described above can be prepared by adjusting the concentration of the reducing agents among the components necessary for protein synthesis, in the reaction solution for the cell-free translation system. There are no particular restrictions on the reducing agent, and at least one may be chosen from well-known reducing agents that have conventionally been used for cell-free protein synthesis reaction solutions, such as dithiothreitol (hereinafter also referred to as "DTT"), 2-mercaptoethanol, glutathione/oxidized glutathione, thioredoxin, lipoic acid, or cystein. For example, for a reaction solution pH of approximately 7.6, when the reducing agent is DTT alone, the final concentration is 20 µM to 70 µM, and preferably 30 µM to 50 µM; when the reducing agent is 2-mercaptoethanol alone, the final concentration is 0.05 mM to 0.5 mM, and preferably 0.1 mM to 0.2 mM; and when the reducing agent is glutathione/oxidized glutathione alone, the final concentration is 10 µM to 400 µM/1 µM to 40 µM, and preferably 30 µM to 50 µM/1 µM to 5 µM.

The concentration of the reducing agent in the weakly reducing synthesis reaction solution of the present invention is not limited to that described above and can be suitably modified according to the protein which is to be synthesized or according to the cell-free protein synthesis system used. There are no particular restrictions on the method for selecting the optimal concentration range for the reducing agent in the weakly reducing protein synthesis reaction solution described above, but examples include methods characterized by making judgments according to the solubilization rate of the proteins synthesized and the effect of substances that catalyze disulfide bond exchange reactions (refolding reactions) on this solubilization. Specifically, methods may comprise steps (1) to (4) as described below:

(1) performing a translation reaction with a plurality of cell-free protein synthesis reaction solutions each comprising a different concentration of a reducing agent, followed by measuring the solubilization rate of the synthesized proteins in the reaction solution;

(2) performing translation reactions with a plurality of cell-free protein synthesis reaction solutions, which are the same as described above in (1), other than the fact that substances catalyzing disulfide bond exchange reactions have been added, followed by measuring the solubilization rate of the synthesized proteins in the reaction solution;

(3) comparing the solubilization rates measured above in (1) and (2); and (4) selecting the concentration range for the reducing agent at which the solubilization rate is increased by the presence of the substance catalyzing the disulfide bond exchange reaction and the concentration range showing, in the absence of the substance, a solubilization rate greater than or equal to the solubilization range for the aforementioned concentration range in the presence of the substance.

In other words, first a plurality of cell-free protein synthesis reaction solutions are prepared at varying concentrations of reducing agent, then a substance catalyzing a disulfide bond exchange reaction is added so as to synthesize protein having at least one intramolecular disulfide bond. Furthermore, as a control experiment, cell-free protein synthesis reaction solutions are prepared, which are the same with the exception of the fact that these do not contain the substance catalyzing the disulfide bond exchange reaction, and translation reactions are performed therewith. In each of the various cases described above, the solubilization rate for the synthesized protein in the reaction solution following the translation reaction is measured. There are no particular restrictions on the method for measuring the solubilization rate but this can, for example, be measured by separating the solubilized protein component of the reaction solution by methods such as centrifugation, and measuring the volumetric ratio of the solubilized component as a percentage of the total reaction solution (using a liquid scintillation counter or autoradiography). The results of these measurements of solubilization rates are used in selecting the optimal reducing agent concentration range for the cell-free protein synthesis reaction solution allowing for protein synthesis wherein intramolecular disulfide bonds are retained, at which the solubilization rate is increased by the presence of a substance catalyzing the disulfide bond exchange reaction and, in some cases, the reducing agent concentration range at which, in the absence of this substance, the solubilization is greater than or equal to the solubilization in the aforementioned concentration range in the presence of the substance. Herein, the solubilization rate is determined to have been increased by the presence of a substance that catalyzes the disulfide bond exchange reaction if the solubilization rate is significantly greater as compared to the solubilization rate following the translation reaction in the control experiment with a cell-free protein synthesis reaction solution containing the same concentration of reducing agent. Note that the preferred reaction solution solubilization rate, in the concentration range wherein the solubilization rate is raised by the presence of a substance catalyzing the disulfide bond exchange reaction, is no less than 50%, and no less than 60% is more preferred.

There are no particular restrictions on the "substance catalyzing the disulfide bond exchange reaction," but use can be made of protein disulfide isomerase (PDI), which is an enzyme found in the endoplasmic reticula of eukaryotic cells, or GroEL and GroES, which are chaperone proteins derived from *E. Coli*, or various proteins that catalyze refolding reactions, such as DnaK, DnaJ and GrpE, or low molecular weight mimics thereof (such as BMC, which is a PDI mimic (*Chem Biol.*, 6. 871-879, (1999)), aromatic thiol compounds (4-mercaptobenzene acetate; *J. Am. Chem. Soc.* 124, 3885-3892 (2002)). Among these, the use of protein disulfide isomerase, which plays a role in the protein refolding mechanism in eukaryotic cells, is preferred.

Furthermore, in the present invention, a more preferable concentration range can be selected by measuring the amounts of protein synthesized in the various cell-free protein synthesis reaction solutions containing reducing agents at the concentration ranges selected as described above, and selecting the concentration range for the reducing agent at which the amount of protein synthesized is the greatest, so as to select the concentration range for the reducing agent at which the greatest amount of protein is synthesized.

Methods of preparing the weakly reducing synthesis reaction solution of the present invention as described above include methods wherein a cell extract for cell-free protein synthesis, which does not contain a reducing agent, is prepared and a reducing agent is added at the concentration range described above, together with the components necessary for cell-free protein synthesis, as well as methods wherein a reducing agent is removed from a cell extract for cell-free protein synthesis which contains the reducing agent, so as to obtain the concentration range described above. Normally, methods wherein the reducing agent is removed from the solution after extraction are preferred due to the simplicity thereof, because high reducing conditions are necessary when the cell extract for cell-free protein synthesis is extracted. Examples of such methods include gel filtration and dialysis. For example, in the case of gel filtration, preparation methods include those wherein, following extraction, the cell extract for cell-free protein synthesis that contains the reducing agent is passed through a gel filtration support, which has been pre-equilibrated with a buffer solution that does not contain the reducing agent, or which contains the reducing agent at a lower concentration. Specifically, a Sephadex G-25 column (Amersham Biosciences) is suitable for use as the gel filtration support. Furthermore, there are no particular restrictions on the composition of this buffer solution that does not contain the reducing agent, or that contains the reducing agent at a lower concentration, and conventional well-known compositions can be suitably selected according to the type of the cell extract being used for the cell-free protein synthesis. For instance, examples are described hereinafter of buffer solutions containing HEPES-KOH, potassium acetate, magnesium acetate, or L-amino acids.

The present invention also provides a cell-free protein synthesis method using the weakly reducing synthesis reaction solution described above. The protein synthesis method of the present invention is characterized in that a translation reaction is performed using a cell-free protein synthesis reaction solution comprising a reducing agent at the concentration range selected by the selection method described above (which is to say, using the weakly reducing synthesis reaction solution described above). Examples of the weakly reducing synthesis reaction solution used include a cell-free protein synthesis reaction solution comprising, as a reducing agent, DTT at a final concentration, with a pH of approximately 7.6, of 20 µM to 70 µM (preferably, 30 µM to 50 µM), a cell-free protein synthesis reaction solution comprising, as a reducing agent, 2-mercaptoethanol at a final concentration of 0.05 mM to 0.5 mM (preferably, 0.1 mM to 0.2 mM), and a cell-free protein synthesis reaction solution comprising, as a reducing agent, glutathione/oxidized glutathione at a final concentration of 10 µM to 400 µM/1 µM to 40 µM (preferably, 30 µM to 50 µM/1 µM to 5 µM), as described above.

Furthermore, in the protein synthesis method of the present invention, it is preferable that the translation reaction be performed by further adding a substance catalyzing a disulfide bond exchange reaction to the weakly reducing synthesis reaction solution described above. By these means, it is possible to more efficiently synthesize protein in which at least one intramolecular disulfide bond is properly formed (retained). Substances such as those described above can be used as the substance catalyzing the disulfide bond exchange reaction without particular restrictions, but the use of protein disulfide isomerase is preferred.

There are no particular restrictions on the amount of this substance that is added, and this may be suitably selected according to the type of substance used, the composition of the cell extract for cell-free protein synthesis, the type of reducing agent, the concentrations, and the like. For example, using a cell extract for cell-free protein synthesis that was extracted from wheat embryo, if protein disulfide-isomerase is added to the cell-free protein synthesis reaction solution, which comprises, as a reducing agent, 20 µM to 70 µM of DTT, and preferably 30 µM to 50 µM of DTT, this protein disulfide-isomerase is added so as to obtain a final concentration in the range of 0.01 µM to 10 µM, and preferably a concentration of 0.5 µM.

Note that, in cases where the substance catalyzing the disulfide bond exchange reaction is added, this may be added either before the start of the translation reaction using the cell-free protein synthesis reaction solution, or after this starts, but in terms of the efficiency with which disulfide bonds are formed, it is preferable that this be added at the beginning of the translation reaction (within 30 minutes of the start of the translation reaction). The cell-free protein synthesis reaction solution containing the substance catalyzing the disulfide bond exchange reaction may also be prepared immediately before the start of the reaction.

(2) Preparation of Cell Extract for Cell-Free Protein Synthesis

Any cell extract may be used to prepare the cell extract for cell-free protein synthesis of the present invention (hereinafter also referred to simply as "cell extract") so long as it has protein synthesis capability in a cell-free protein synthesis system. Specific examples of cell extracts that can be used in the present invention include known cell extracts, such as those from *E. coli*, plant seed embryo and rabbit reticulocytes. Commercially available cell extracts may be used, or these may be prepared according to methods known per se and specifically, for *E. coli* extracts, that described in Pratt, J. M. et al., *Transcription and Translation*, Hames, B. D. & Higgins, S. J., eds., IRL Press, Oxford (1984).

Commercially available cell extracts include: the *E. coli* S30 Extract System (Promega) and the RTS 500 Rapid Translation System (Roche) and the like, which are derived from *E. coli*; the Rabbit Reticulocyte Lysate System (Promega) and the like, which are derived from rabbit reticulocytes; and PROTEIOS™ (TOYOBO) and the like, which are derived from wheat embryo. From among these, the use of plant seed embryo extracts is preferred, and the seeds of members of the Gramineae family, such as wheat, barley, rice, and corn, are preferred as plant seeds. From among these, the use of wheat embryo extract is suitable as the cell extract of the present invention.

Examples of methods for preparing a wheat embryo extract include those described in Johnston, F. B., et al., *Nature*, 179, 160-161 (1957), or Erickson, A. H., et al., *Meth. In Enzyimol.*, 96, 38-50 (1996) and the like, and a detailed description is given below.

Ordinarily, the embryo component is extremely small and therefore, in order to obtain the embryo in an efficient manner, it is preferable that components other than embryo be removed to as great an extent as is possible. Normally, mechanical force is first applied to the plant seeds so as to produce a mixture comprising embryo, crushed endosperm and crushed seed coat. The crushed endosperm, crushed seed coat and the like are removed from this mixture, so as to produce a crude embryo fraction (a mixture primarily composed of embryo but also containing crushed endosperm and crushed seed coat). It suffices that the force applied to the plant seed be of a strength sufficient to separate the embryo from the plant seed. Specifically, known grinding equipment is used to grind the plant seeds, so as to produce a mixture containing embryo, crushed endosperm and crushed seed coat.

The plant seeds can be ground using commonly known grinding apparatus but it is preferable to use grinding apparatus of the type that applies impact force to the material that is ground, such as a pin mill or a hammer mill. The degree of grinding maybe suitably chosen according to the size of the embryo of the plant seed that is used. For example, wheat grain is usually ground to a maximum length of no greater than 4 mm, and is preferably ground maximum length of no greater than 2 mm. Furthermore, it is preferable t hat the grinding be performed as dry grinding.

Next, a crude embryo fraction is recovered from the ground plant seed produced, using the well-known classifier, such as a sieve. For example, in the case of wheat grain, a crude embryo fraction is recovered using a mesh sieve of a 0.5 to 2.0 mm, and preferably 0.7 to 1.4 mm. Furthermore, if necessary, the seed coat, the endosperm, dust and the like contained in the crude embryo fraction produced can be removed by wind force or electrostatic force.

It is also possible to produce a crude embryo fraction using methods that make use of the difference in the specific gravities of embryo, seed coat and endosperm, such as heavy media separation. In order to obtain a crude embryo fraction containing a greater quantity of embryo, a plurality of the methods described above may be combined. Furthermore, it is possible to select the embryo from the crude embryo fraction produced, for example, either visually or using a color sorter, or the like.

As an endosperm component may adhere to the embryo fraction produced in this manner, it is normally preferable that this be washed in order to purify the embryo. It is preferable that this be washed by dispersing/suspending the embryo fraction in cold water or a cold aqueous solution at a temperature that is normally no greater than 10° C. and preferably no greater than 4° C. and washed until the washing solution is no longer clouded. It is more preferable that the embryo fraction be dispersed/suspended in an aqueous solution containing a surfactant, which is normally at a temperature of no more than 10° C. and preferably at a temperature of no more than 4° C., and washed until the washing solution is no longer clouded. It is preferable that the surfactant be nonionic, and a wide variety of surfactants can be used so long as these are nonionic. Specific examples of suitable substances include Brij, Triton, Nonidet P40, Tween, and the like, which are polyoxyethylene derivatives. From among these, Nonidet P40 is the most suitable. These nonionic surfactants can be used at concentrations sufficient to remove the endosperm component but which do not negatively impact the protein synthesis activity of the embryo component. For example, a concentration of 0.5% can be used. The washing treatment may be either one of washing with water or an aqueous solution, or washing with a surfactant. Alternatively, the two may be used together. Furthermore, this washing may be combined with sonication.

In the present invention, after selecting the plant embryo from the ground product, which was produced by grinding the plant seed as described above, the intact (capable of germinating) embryo produced by washing is minced (preferably in the presence of an extracting solvent) whereafter the wheat embryo extract produced is separated and further purified, to produce a wheat embryo extract for cell-free protein synthesis.

In terms of the extracting solvent, aqueous solutions containing a buffer solution (for example, N-2-hydroxyethylpiperazine-N'-2'-ethanesulfonic acid (HEPES)-KOH, piperazine-1,4'-bis(2-ethanesulfonic acid) (PIPES)-NaOH, tris (hydroxymethyl)aminomethane (Tris)-HCl and the like, at a pH of 5 to 10), potassium ions, magnesium ions, and/or thiol reducing agents can be used. There are no particular restrictions on the thiol reducing agents but examples include DTT, 2-mercaptoethanol, glutathione/oxidized glutathione, thioredoxin, lipoic acid, cystein and the like. The concentrations for these reducing agents can be suitably selected according to the kind of reducing agent and can, for example, be selected within the ranges of, for DTT, 10 µM to 5 mM, for 2-mercaptoethanol, 50 µM to 20 mM, and for glutathione/oxidized glutathione, 5 µM to 1 mM/1 µM to 100 µM. Furthermore, calcium ions and L-amino acids and the like may be added as necessary. For example, solutions containing HEPES-KOH, potassium acetate, magnesium acetate, or L-amino acids or solutions wherein the method of Patterson et al. is partially modified (a solution containing HEPES-KOH, potassium acetate, magnesium acetate, calcium chloride, L-amino acids and/or DTT) can be used as the extracting solvent. The compositions and concentrations of the various components in the extracting solvent are already known per se, and compositions and concentrations commonly used in the preparation of wheat embryo extracts for cell-free protein synthesis may be adopted.

The embryo is mixed with an amount of extracting solvent sufficient for extraction thereof and the embryo is minced in the presence of the extracting solvent. In terms of the amount of extracting solvent used for each gram of unwashed embryo, this is normally no less than 0.1 ml, preferably no less than 0.5 ml, and more preferably no less than 1 ml. There is no particular upper limit on the amount of extracting solvent, but this is normally no more than 10 ml, and preferably no more than 5 ml, for each gram of unwashed embryo. Furthermore, in terms of the embryo which is to be minced, this may be frozen as conventional, or an unfrozen embryo may be used, but the use of unfrozen embryo is preferred.

In terms of the mincing method, conventional well-known methods, such as milling, crushing, impact or chopping may be used as the grinding method, but methods of mincing embryo by impact or chopping are preferred. Herein, the expression "mincing by impact or chopping" means breaking down the plant embryo under conditions that minimize, as compared to conventional milling or crushing, the breakdown of parts of the plant embryo such as cellular membranes, cell walls, and organelles such as mitochondria, chloroplasts and the cell nucleus, and the like.

There are no particular restrictions on the apparatus and methods that can be used in mincing the embryo, so long as the conditions described above are satisfied, but it is preferable that devices having a high-speed rotary blade, such as a Waring blender, be used. The speed of the rotating blade is normally no less than 1,000 rpm and preferably no less than 5,000 rpm, but is normally no greater than 30,000 rpm, and preferably no greater than 25,000 rpm. The running time for the rotating blade is normally no less than five seconds and preferably no less than 10 seconds. There is no particular upper limit on the running time, but this is normally no more than 10 minutes and preferably no more than five minutes. The temperature during mincing is preferably no greater than 10° C. and is within a temperature range in which the mincing operation is possible. On the order of 4° C. is particularly preferable.

As a result of mincing the embryo by impact or chopping in this manner, the cell nucleus and cell walls of the embryo are not completely destroyed, but rather at least some portion thereof remains without having been broken down. That is to say, as the cellular membranes, cell walls and organelles such as the cell nucleus, and the like, of the embryo are not broken down a greater degree than is necessary, it is possible to efficiently extract substances necessary to protein synthesis, such as RNA, ribosomes and the like, which are localized within the cytoplasm, at high degrees of purity, without contamination by impurities contained therein, such as and lipids and DNA.

According to such a method, the conventional step of grinding the plant embryo and the conventional step of mixing the wheat embryo which has been grinded with an extracting solvent are carried out simultaneously, whereby wheat embryo extract can be produced efficiently. The method described above is also referred to as the "blender method."

It is preferable that such mincing of the plant embryo, and in particular mincing by impact or chopping, be performed in the presence of an extracting solvent, but it is also possible to add the extracting solvent after mincing.

Next, the wheat embryo extract is recovered by centrifugation or the like and purified by gel filtration, dialysis or the like, allowing for the production of wheat embryo extract. Gel filtration may, for example, be performed using a Sephadex G-25 column or the like. The compositions and concentrations of the various components in the gel filtration solution are already known per se, and compositions and concentrations commonly used in the preparation of wheat embryo extracts for cell-free protein synthesis may be adopted. Here, if a cell extract for cell-free protein synthesis is extracted under the highly reducing conditions described above, it is preferable that this cell extract be passed through a gel filtration support that has been pre-equilibrated with a buffer solution that does not contain the reducing agent or which contains the reducing agent at a lower concentration. There are no particular restrictions on the composition of the buffer solution, but the use of a solution containing HEPES-KOH (pH 7.6), potassium acetate, magnesium acetate or L-amino acids is preferred, as this absorbs approximately 97% of the reducing agent contained in the extract solution. Specifically, if extraction was performed on wheat embryo using an extract solution containing 1 mM of DTT as the reducing agent, a wheat embryo extract containing approximately 30 μM of DTT, as the final concentration, can be obtained. However, as the activity of wheat embryo extract having a lower concentration of reducing agent is made markedly inferior as a result of frozen storage, it is preferable that the process of removing the reducing agent be performed immediately before this is used in the translation reaction.

Following gel filtration or dialysis, the embryo extract may be contaminated with microorganisms, and in particular, with spores such as those of filamentous bacteria (mold). It is, therefore, preferable that these microorganisms be eradicated. Particularly, the proliferation of microorganisms is sometimes observed in long-term (more than one day) cell-free protein synthesis reactions. It is, therefore, important to prevent this. There are no particular restrictions on the means for eradicating microorganisms, but the use of antimicrobial filters is preferred.

There are no particular restrictions on the pore size for the filter, so long as this is a size capable of eradicating microorganisms with which the cell extract may be contaminated, but 0.1 to 1 μm is normally suitable and 0.2 to 0.5 μm is preferred. It is of note that the spore size of *Bacillus subtilis*, which is of the small class, is 0.5 μm×1 μm and therefore the use of a 0.20 μm filter (for example the Minisart™ by Sartorius) is effective in removing spores. When filtering, it is preferable that a filter having a large pore size be used first, whereafter a filter having a pore size capable of eliminating microorganisms by which the cell extract may be contaminated is used.

The cell extract for cell-free protein synthesis obtained in this manner is purified so as to substantially completely remove endosperm that comprises substances, contained or retained by the source cell itself, which inhibit protein synthesis function (substances that act on mRNA, tRNA, translation factor proteins, ribosomes and the like so as to inhibit the function thereof such as tritin, thionine, ribonuclease and the like). Herein, the expression "purified so as to substantially completely remove endosperm" refers to wheat embryo extracts from which endosperm components have been removed to an extent that ribosomes are substantially not deadenylated. Furthermore, the expression "to an extent that ribosomes are substantially not deadenylated" means that the ribosome deadenylation is less than 7%, and preferably 1% or less.

Furthermore, such cell extract for cell-free protein synthesis contains low molecular weight substances that inhibit protein synthesis (hereinafter these are also referred to as "low molecular weight synthesis inhibitors"). Therefore, it is preferable that these low molecular weight synthesis inhibitors be removed by fractionation from the constituent components of the cell extract, based on differences in molecular weight. It suffices that the molecular weight of the substances to be eliminated (low molecular weight synthesis inhibitors) be less than that of the factors contained within the cell extract that are necessary to protein synthesis. Specifically, examples of molecular weights include those which are no greater than 14,000 to 50,000 Daltons, and preferably no greater than 14,000 Daltons.

Commonly used methods, which are well-known per se, can be used as the method for eliminating the low molecular weight synthesis inhibitors from the cell extract, and specific examples include methods based on dialysis by way of a dialysis membrane, gel filtration, ultrafiltration and the like. From among these, methods based on dialysis (dialyzing) are preferred for such reasons as the ease of supplying the substance to the internal dialysis solution. Note that, the expression "free of" low molecular weight synthesis inhibitors means free of low molecular weight synthesis inhibitors to as great an extent as is true for solutions having been processed by the various methods described above so as to eliminate low molecular weight synthesis inhibitors, and whether or not these have been eliminated can be verified by way of the amount of protein synthesis activity in the cell extract produced.

Hereinafter, an example of the use of dialysis is described in detail.

Examples of dialysis membranes which can be used for dialysis include those having molecular weight cutoff of 50,000 to 12,000 Daltons. Specifically, the use of a regenerated cellulose membrane having a molecular weight cutoff of 12,000 to 14,000 Daltons (Viskase Sales, Chicago) and the Spectra/Pore 6 (Spectrum Laboratories Inc., CA, USA) having a molecular weight cutoff of 50,000, is preferred. A suitable amount of the aforementioned cell extract is placed within such a dialysis membrane and dialysis is performed according to normal methods. It is preferable that the period of time for which dialysis is performed be on the order of 30 minutes to 24 hours.

When the low molecular weight synthesis inhibitors are eliminated, in cases where insoluble matter forms in the cell extract, by means of inhibiting this (hereinafter also referred to as "stabilizing the cell extract"), it is possible to increase the protein synthesis activity of the final cell extract obtained (hereinafter also referred to as "processed cell extract"). Here, insoluble matter is matter recovered as a precipitate from the cell extract in a step of eliminating low molecular weight synthesis inhibitors under suitable conditions, and specifically, by centrifuging, filtering or the like, and particularly by centrifuging at approximately 10,000 to 80,000× g, and preferably 30,000×g, for approximately 5 to 60 minutes, and preferably 20 minutes.

Specific methods for stabilizing the cell extract include methods wherein the elimination of the low molecular weight inhibitors is performed in a solution containing at least high-energy phosphate compounds, such as ATP, GTP or the like. The use of ATP as the high-energy phosphate compound is preferred. Furthermore, it is preferable that this be performed in a solution containing ATP and GTP, and more preferable that this be performed in a solution containing ATP, GTP and the 20 types of amino acids.

When the low molecular weight synthesis inhibitors are to be eliminated from a solution containing these components (hereinafter also referred to as "stabilizing components"), the stabilizing components may be added to the cell extract beforehand, and this may be supplied to the process for eliminating low molecular weight synthesis inhibitors after incubation. If dialysis is used for the elimination of low molecular weight synthesis inhibitors, the low molecular weight synthesis inhibitors can be eliminated by dialyzing with stabilizing components added not only to the cell extract, but also to the external dialysis solution. Adding a stabilizing component to the external dialysis solution is preferable as, even if the stabilizing component is broken down during dialysis, a new stabilizing component is continuously supplied. This can also be applied when gel filtration or ultrafiltration is used, and the same effect can be achieved by equilibrating the various supports with a filtration buffer solution containing a stabilizing component, whereafter a cell extract containing the stabilizing component is supplied and filtration is performed by adding more of the buffer solution.

The amount of stabilizing component to be added and the time for the stabilization treatment may be suitably chosen according to the type of cell extract and the preparation method. Methods for selecting the same include those wherein various different amounts and types of stabilizing component are experimentally added to the cell extract and, after a suitable amount of time, the process for eliminating low molecular weight synthesis inhibitors is performed, whereafter the soluble fraction and the insoluble fraction are separated by such methods as centrifuging the processed cell extract produced, and the stabilizing component for which the least amount of insoluble matter was formed is chosen. Furthermore, a method is also preferred wherein the processed cell extracts obtained are used to perform cell-free protein synthesis, and a cell extract having high protein synthesis activity is chosen. Furthermore, the selection methods described above also include methods wherein, in cases where dialysis is used for the process of eliminating low molecular weight synthesis inhibitors, suitable stabilizing components are added also to the external dialysis solution and dialysis is performed for a suitable period of time using these, whereafter selection is made according to the amount of insoluble matter in the cell extract or the protein synthesis activity of the cell extract produced and the like.

Specific examples of stabilization conditions for cell extracts selected in this manner include, in the case of eliminating low molecular weight synthesis inhibitors by way of dialysis with the wheat embryo extract prepared using the blender method, adding 100 µM to 0.5 mM of ATP, 25 µM to 1 mM of GTP and 25 µM to 5 mM of each of the 20 types of L-amino acid to the wheat embryo extract and the external dialysis and dialyzing for 30 minutes to 1 hour or more. If dialysis is used, this may be performed at any temperature, so long as it is a temperature that does not impair protein synthesis activity and at which dialysis is possible. Specifically, the minimum temperature is a temperature at which the solution does not freeze, normally −10° C. and preferably −5° C., and the maximum temperature is the limit for avoiding negative impact on the solution used for dialysis, which is 40° C. and preferably 38° C.

There are no particular restrictions on the method for adding the stabilizing component to the cell extract, but this may be added before the process for eliminating low molecular weight synthesis inhibitors, incubated for a suitable period of time so as to achieve stabilization, whereafter the process for eliminating low molecular weight synthesis inhibitors may be performed. Alternatively the process for eliminating low molecular weight synthesis inhibitors may performed using a cell extract to which the stabilizing component has been added and/or using a buffer solution to which this stabilizing component has been added for the purpose of use in this elimination process.

(3) Protein Synthesis Using the Weakly Reducing Synthesis Reaction Solution

Protein synthesis may be performed with the cell extract for cell-free protein synthesis described above by adjusting the concentration range of reducing agent to the range described above in (1), adding the energy source, amino acids, translation template or tRNA and the like necessary for the cell-free protein synthesis, as well as the substance catalyzing the disulfide bond exchange reaction, as necessary, and in the case of a cell-free transcription/translation system, further adding enzymes necessary to transcription, such as RNA polymerase and the four types of nucleoside triphosphate, and the transcription template DNA in place of the translation template, so as to prepare a cell-free protein synthesis reaction solution, which is placed in a system or an apparatus well known per se that has been separately selected. Systems and apparatus for protein synthesis include the batch method (Pratt, J. M. et al., *Transcription and Translation*, Hames, 179-209, B. D. & Higgins, S. J., eds., IRL Press, Oxford (1984)), or the continuous cell-free protein synthesis system, which continuously supplies the amino acids, the energy source and the like to the reaction system (Spirin, A. S., et al., *Science*, 242, 1162-1164 (1988)), the dialysis method (Kikawa et al., 21st Meeting of The Molecular Biology Society of Japan, WID6), or the overlay method (manufacturer's instructions for PROTEIOS™ Wheat embryo cell-free protein synthesis core kit, TOYOBO).

Furthermore, such methods may be used as those wherein the template RNA, the amino acids, the energy source and the like are supplied to the synthesis reaction system when necessary, and the synthesis products and breakdown products are removed when necessary (JP-2000-333673-A, hereinafter also referred to as "discontinuous gel filtration")).

From among these methods, the use of systems that continuously or discontinuously supply amino acids and an energy source allows the reaction to be maintained over a long period of time, which makes further increases in efficiency possible, but when performing protein synthesis using the weakly reducing synthesis reaction solution of the present invention, the batch method is preferred, as this tends to improve protein synthesis efficiency. Furthermore, if a wheat embryo extract is prepared by the blender method described above in (2), it normally contains a sufficient amount of tRNA, so that it is not necessary to add tRNA.

Furthermore, there are no particular restrictions on the proteins synthesized by the method of the present invention and any type of protein may be synthesized, but it is preferable that these be proteins having at least one intramolecular disulfide bond. This is because, by virtue of the synthesis method of the present invention, even when protein having at least one intramolecular disulfide bond is synthesized in the cell-free protein synthesis system, the three-dimensional structure is properly formed and it is possible to synthesize a protein having substantially the same function as the original function of the protein. Specific examples of proteins having at least one intramolecular disulfide bond that can be advantageously synthesized by the synthesis method of the present invention so as to possess substantially the same function as the function of the original protein include, for example, antibody proteins of antibodies against any antigen, such as Fab fragments and single-chain antibodies in which the $V_L$ and the $V_H$ are ligated by a ring (scFv), or for example, secretory proteins such as serum albumin, acidic phosphatase, insulin, lysozyme, cellulase, or for example, membrane proteins and the like such as G-protein coupling receptor (GPCR) proteins, glutamic acid transporters localized in the brain, and in terms of hormone receptors, the Leucine Rich Repeat receptor (LRR receptor). If antibody proteins are synthesized, antibody libraries can be constructed by synthesis, using as a template DNA that encodes artificial antibody libraries having random amino acid sequences in the antigen binding region. Furthermore, proteins having an intermolecular disulfide bond, such as for example IgC, wherein the heavy chain and the light chain are joined by a disulfide bond, can be advantageously synthesized by the method of the present invention.

When protein synthesis is performed by way of the batch method, for example, the synthesis reaction solution without a translation template, is pre-incubated for a suitable period of time as necessary, whereafter the translation template is added and protein synthesis is performed by incubation, and the like. In terms of the cell-free protein synthesis reaction solution (translation reaction solution), this may for example contain 10 to 50 mM of HEPES-KOH (pH 7.8), 55 to 120 mM of potassium acetate, 1 to 5 mM of magnesium acetate, 0.1 to 0.6 mM of spermidine, 0.025 to 1 mM of each of the L-amino acids, 20 to 70 µM, preferably 30 to 50 µM of DTT, 1 to 1.5 mM of ATP, 0.2 to 0.5 mM of GTP, 10 to 20 mM of creatine phosphate, 0.5 to 1.0 U/µl of RNase inhibitor, 0.01 to 10 µM of protein disulfide isomerase and 24 to 75% of wheat embryo extract (prepared by the blender method).

When such a translation reaction solution is used, the pre-incubation is at 10 to 40° C. for 5 to 10 minutes and the incubation is likewise at 10 to 40° C., preferably 18 to 30° C., and more preferably 20 to 26° C. The reaction time is the time until the reaction stops, and in the batch method this is normally on the order of 10 minutes to 7 hours.

If protein synthesis is performed by means of the dialysis method, the synthesis reaction solution is made the internal dialysis solution and a device is used whereby this is separated from the external dialysis solution by a dialysis membrane, through which substances can transport, whereby protein synthesis is performed. Specific examples include those wherein the synthesis reaction solution described above, without a translation template, is pre-incubated for a suitable period of time as necessary, whereafter the translation template is added, whereafter this is placed in a suitable dialysis chamber as the internal reaction solution. Examples of dialysis containers include containers with a dialysis membrane at the bottom (Daiichi Kagaku; Dialysis Cup 12,000 or the like), or a dialysis tube (Sanko Junyaku: 12,000 or the like). The dialysis membrane used may have a molecular weight cutoff of 10,000 Daltons or more, those with a molecular weight cutoff on the order of 12,000 Daltons being preferred.

The aforementioned synthesis reaction solution, without the translation template, is used as the external dialysis solution. It is possible to improve dialysis efficiency by replacing the external dialysis solution with fresh dialysis solution when the reaction speed drops. The reaction temperature and time are suitably selected according to the protein synthesis system to be used, but in systems wherein wheat embryo extract is used, this is normally performed at 10 to 40° C., preferably 18 to 30° C., and more preferably 20 to 26° C., for 10 minutes to 12 days.

When the protein synthesis is carried out using the overlay method, the synthesis reaction solution is placed in a suitable container, and the external dialysis solution described above in the dialysis method is overlaid on top of this solution (the synthesis reaction solution) so as not to disturb the interface, so as to carry out the protein synthesis. Specific examples include those wherein the synthesis reaction solution described above, without a translation template, is pre-incubated for a suitable period of time as necessary, whereafter the translation template is added, whereafter this is placed in a suitable container as the reaction phase. Examples of the container include a microtiter plate or the like. The external dialysis solution described above in the dialysis method (supply phase) is overlaid on the top layer of this reaction phase so as not to disturb the interface, and the reaction is performed.

In addition, the interface between the two phases does not have to be formed by superposition in a horizontal plane; a horizontal plane can also be formed by centrifuging a mixture that contains both phases. When the diameter of the circular interface between the two phases is 7 mm, a volume ratio of the reaction phase and the supply phase of 1:4 to 1:8 is suitable, and 1:5 is preferred. The rate of exchange of substances due to diffusion increases with the area of the interface formed by the two phases, increasing the protein synthesis efficiency. Therefore, the volume ratio of the two phases changes according to the area of the interface between the two phases. The synthesis reaction is carried out under static conditions, and the reaction temperature and time are suitably selected for the protein synthesis system to be used, but in systems using wheat embryo extract, this can be performed at 10 to 40° C., preferably 18 to 30° C. and more preferably at 20 to 26° C., normally for 10 to 17 hours. Furthermore, when *E. coli* extract is used, a reaction temperature of 30 to 37° C. is suitable.

When the protein synthesis is carried out using the discontinuous gel filtration method, the synthesis reaction is performed by way of the synthesis reaction solution, and when the synthesis reaction stops, the template RNA, the amino acids, the energy source and the like are supplied, and the products of synthesis or degradation are evacuated, so as to perform protein synthesis. Specific examples include those wherein the synthesis reaction solution described above, without a translation template, is pre-incubated for a suitable period of time as necessary, whereafter the translation template is added, this is placed in a suitable dialysis chamber and the reaction is performed. Examples of the container include a micro plate or the like. In this reaction, when, for example, the reaction solution contains 48% by volume of wheat embryo extract, the synthesis reaction stops completely in 1 hour. This can be verified by measuring the incorporation of amino acids into the protein or by an analysis of polyribosomes by centrifugation over a sucrose density gradient (*Proc. Nat'l. Acad. Sci.* USA, 97, pp. 559-564 (2000)).

The synthesis reaction solution in which the synthesis reaction has stopped is passed through a gel filtration column, which has been pre-equilibrated with a supply solution that has the same composition as the external dialysis solution described in the dialysis method. The synthesis reaction is resumed by re-incubating the filtered solution at a suitable reaction temperature, and the protein synthesis proceeds over several hours. Thereafter, these reaction and gel filtration operations are repeated. The reaction temperature and time are suitably selected according to the protein synthesis system to be used, but in systems wherein wheat embryo extract is used, gel filtration is preferably repeated once every hour at 26° C.

The proteins obtained in this way can be identified by a method known per se. Specific examples include: measurement of amino acids incorporated into proteins; separation by SDS-polyacrylamide electrophoresis and staining with Coomassie brilliant blue (CBB); autoradiography (Endo, Y., et al., *J. Biotech.*, 25, 221-230 (1992)); *Proc. Nat'l. Acad. Sci.* USA, 97, 559-564 (2000)) and the like.

Furthermore, as the reaction solution produced in this manner contains a high concentration of the target protein, the target protein can easily be obtained from the reaction solution by separation and purification methods well-known per se, such as dialysis, ion exchange chromatography, affinity chromatography, gel filtration, and the like.

In the following, the present invention is described in further detail by way of experiments, but the following experiments are only intended to aid in concrete appreciation of the present invention, and the scope of the present invention is in no way limited to the experiments described below.

EXPERIMENT 1

Preparation of Wheat Embryo Extract

Hokkaido Chihoku wheat grain (not disinfected) was added to a mill (Fritsch: Rotor Speed Mill Pulverisette 14) at a rate of 100 g per minute, and the grain was moderately ground at a rotation speed of 8,000 rpm. After recovering a fraction containing germinatable embryos with a sieve (mesh size 0.7 to 1.00 mm), the surfacing fraction containing the germinatable embryos was recovered by flotation using a mixture of carbon tetrachloride and cyclohexane (volume ratio=carbon tetrachloride:cyclohexane=2.4:), the organic solvent was eliminated by desiccation at room temperature, and then impurities such as seed coat were eliminated by air-blowing at room temperature to obtain a crude embryo fraction.

Next, a belt type color sorter BLM-300K (Manufacturer: Anzai Manufacturing Co., Ltd., Marketed by Anzai Co., Ltd.) was used to select the embryo from the crude embryo fraction by way of color difference, as follows. This color sorter is a device comprising: means for irradiating the crude embryo fraction with light; means for detecting reflected light and/or transmitted light from the crude embryo fraction; means for comparing the detected value with a standard value; and means for selectively eliminating that which is outside the standard value or that which is within the standard value.

The crude embryo fraction was supplied onto the color sorter belt so as to produce 1000 to 5000 particles/m$^2$, the crude embryo fraction on the belt was irradiated with fluorescent light, and the reflected light was detected. The belt transport speed was 50 m/minute. A monochrome CCD line sensor (2048 pixels) was used as the photosensor.

First, in order to eliminate components darker than the embryo (seed coat and the like), a beige colored belt was used and the standard value was set between the brightness of the embryo and seed coat and objects outside of the standard value were removed by suctioning. Next, in order to select the endosperm, a dark green belt was used and the standard value was set between the brightness of the embryo and endosperm, and objects outside of the standard value were removed by suctioning. Suctioning was performed by way of 30 suction nozzles (the suction nozzles were aligned with one suction nozzle for each centimeter of length) positioned approximately 1 cm above the transport belt.

By repeating this process, the embryo was selected to a embryo purity (weight ratio of embryo per gram in any sample) of no less than 98%.

The wheat embryo fraction obtained was suspended in distilled water at 4° C., and washed using an ultrasonic cleaner until the washing solution was no longer clouded.

This was then suspended in a 0.5% (volume) Nonidet (Nacalai Tectonics) P40 solution and washed using an ultrasonic washing apparatus until the washing solution was no longer clouded, so as to obtain the wheat embryo, whereafter operations were performed at 4° C.

Two volumes of extracting solvent (80 mM of HEPES-KOH (pH 7.8), 200 mM of potassium acetate, 10 mM of magnesium acetate, 8 mM of dithiothreitol, (0.6 mM of each of the 20 kinds of L-amino acids may be added) were added with respect to the wet weight of the washed embryo, and the embryo was subject to limited grinding in a Waring blender three times, for 30 seconds each, at 5,000 to 20,000 rpm. The centrifugation supernatant obtained from this homogenate by centrifuging in a high-speed centrifuge for 30 minutes at 30,000×g was centrifuged again under the same conditions, and the supernatant was collected. The activity of this sample was not observed to drop with long term storage at no greater than −80° C. The supernatant collected was passed through a filter having a pore size of 0.2 µm (NEW Steradisc 25; Kurabo Industries Ltd.) so as to perform filtration sterilization and remove micro contaminants.

Next, this filtrate was subject to gel filtration using a Sephadex G-25 column that had been pre-equilibrated with a buffer solution that did not contain the reducing agent (40 mM of HEPES-KOH (pH 7.8), 100 mM of potassium acetate, 5 mM of magnesium acetate, and a mixed solution of 0.3 mM of each of the 20 kinds of L-amino acids (depending on the protein synthesis objective, amino acids may be omitted or labeled amino acids may be added). The resulting filtrate was once again centrifuged for 30 minutes at 30,000×g and the concentration of the supernatant recovered was adjusted so that the $A_{260}$ was 90 to 150 ($A_{260}/A_{280}$=1.4 to 1.6), after which it was stored at no greater than −80° C. until it was used in the dialysis treatment and protein synthesis reaction described below.

EXPERIMENT 2

Analysis of the Antigen Binding of Single-Chain Antisalmonella Antibody Synthesized Using a Weakly Reducing Cell-Free Protein Synthesis Reaction Solution (1) Construction of DNA Encoding Wild-Type and Mutant Salmonella Single-Chain Antibodies Single-chain antisalmonella antibodies having at least one intramolecular disulfide bond were selected as the target for the protein synthesis of the present invention. The x-ray structure of this antibody has already been analyzed and detailed studies have been conducted into molecular recognition of carbohydrate chains (Cygler, M., et al., *Science*, 253, 442-445 (1991); Bundle, D. R. et al, *Biochemistry*, 33, 5172-5182 (1994)). Lipopolysaccharides are present on the cell surface of the salmonella bacterium and the antisalmonella antibody binds to an O-antigen positioned the furthest outside the cell on these lipopolysaccharides (Anand, N. N., et al., *Protein Engin.*, 3, 541-546 (1990)). It has been reported that large amounts of a single-chain antibody wherein the $V_L$ chain and the $V_H$ chain, which are antigen recognition sites that bind specifically to the O-antigen, are ligated by a specific ring (linker) have been expressed in *E. coli* (Anand, N. N., et al., *J. Biol. Chem.*, 266, 21874-21879 (1991)). To synthesize a single-chain antibody in an active state, the formation of disulfide bonds, one of which being present in each of the $V_L$ chain and the $V_H$ chain, is indispensable (Zdanov, A. L. Y., et al., *Proc.*

*Nat'l. Acad. Sci. USA.*, 91, 6423-6427 (1994)), which is why these single-chain antibodies were selected as a target for the protein synthesis method of the present invention.

The DNA which encodes the single-chain antisalmonella antibody was amplified by the polymerase chain reaction (PCR), using as a template a plasmid containing DNA that encodes a single-chain antibody for the wild salmonella O-antigen (Anand, N. N., et al., *J. Biol. Chem.*, 266, 21874-21879 (1991)) and using primers comprising the base sequences set forth in SEQ ID NOs: 1 and 2. The DNA fragment obtained was inserted into a pGEMT-easy vector (Promega), which was subsequently subject to enzymatic restriction with BglII and NotI. The DNA fragment obtained was inserted into a pEU vector which had been subject to the same enzymatic restriction beforehand. This plasmid was used as a template for PCR with primers comprising the base sequences set forth in SEQ ID NOs: 3 and 4, and a stop codon was introduced. The plasmid constructed here was called scfv-pEU.

Furthermore, three-dimensional x-ray structure analysis has shown that, among the six hyper variable loops present in the antigen recognition site of the single-chain antisalmonella antibody, the region which most contributes to antigen binding is the VH3 region, and it has already been reported that the antigen binding activity is greatly reduced by introducing mutations into this region (Brummell, D. A., et al., *Biochemistry*, 32, 1180-1187 (1993)). Then, with the object of analyzing the antigen specificity of the single-chain antibody synthesized by the cell-free protein synthesis system, in order to construct a mutant single-chain antisalmonella antibody having a mutation introduced into this region, DNA serving as a template for this antibody was constructed.

DNA was constructed which encodes a mutant wherein all nine of the amino acids in the VH3 region are substituted with alanine (hereinafter this is sometimes referred to as "AlaH3"). First, using the scfv-pEU plasmid constructed as described above as a template and using primers comprising the base sequences set forth in SEQ ID NOs: 5 and 6, PCR was performed with a LA taq (TAKARA) kit. The PCR reaction solution was prepared as 5 µl of 10× LA buffer, 5 µl of 25 mM magnesium chloride, 8 µl of 2.5 mM dNTP, 1 µl of each of the primers at 20 µM, and 0.1 ng template plasmid/50 µl and the reaction was performed at 94° C. for 1 minute×1 cycle, 94° C. for 45 seconds/55° C. for 1 minute/72° C. for 1.5 minutes×30 cycles, and 72° C. for 5 minutes. The amplified DNA fragment was blunt-ended using KOD T4 polymerase (NEB) according to conventional methods, whereafter, following phosphorylation with Polynucleotide kinase (NEB), self ligation was performed using Ligation High (TOYOBO), to construct a circular plasmid (hereinafter sometimes referred to as "AlaH3-pEU").

Furthermore, a mutant (hereinafter sometimes referred to as "G102D") wherein a glycine residue, which is a key component in the structural formation of the hyper variable loops located in the antigen recognition site of the single-chain antisalmonella antibody, was substituted by an aspartic acid, was amplified by PCR in the same manner as described above, using primers comprising the base sequences set forth in SEQ ID NOs: 7 and 8, to produce DNA which was used to construct a circular plasmid (hereinafter sometimes referred to as "G102D-pEU").

(2) Protein Synthesis Using the Weakly Reducing Synthesis Reaction Solution

A transcription reaction was performed using SP6 RNA polymerase (TOYOBO) with the template DNA obtained above in (1). The reaction solution comprised 80 mM of HEPES-KOH (pH 7.6), 16 mM of magnesium acetate, 2 mM of spermidine, 10 mM of DTT, 2.5 mM of each of the NTPs, 0.8 U/μl of RNase inhibitor, 50 μg/ml plasmid, and 1.2 U/μl of SP6 RNA polymerase/ddw 400 μl. After incubating for two hours at 37° C., phenol/chloroform extraction was performed, this was purified with a NICK column (Amersham Pharmacia) and ethanol precipitated, and the precipitate was dissolved in 35 μl of purified water.

A translation reaction was performed using the mRNA produced as the translation template. In terms of the composition of the weakly reducing synthesis reaction solution, a mixture was used wherein 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/μl of RNase inhibitor (Promega), 4 nCi/μl of $^{14}C$-Leu, and 7.5 μg of mRNA were added to 12 μl of the gel filtered wheat embryo extract described above in Experiment 1. Note that the redox potential of the weakly reducing synthesis reaction solution was −14 mV (measured using the ORP controller FO-2000 (EYELA)) according to the operation manual provided by the manufacturer: for example by preparing approximately 3 ml of synthesis reaction solution, incubating at 26° C., immersing electrodes for measuring the electrical potential in the solution, then waiting for the measured value to stabilize) and the final concentration of DTT was 58 μM. The translation reaction was performed at 26° C. for 4 hours, using the batch method.

At 1 hour intervals during the translation reaction, 5 μl was spotted on a Whatman filter, whereafter this was TCA precipitated and the amount of $^{14}C$-Leu incorporated into each of the spots was measured using a liquid scintillation counter. The results are shown in FIG. 1. As can be seen in FIG. 1, the amount synthesized for both the wild-type and the mutant single-chain antibody reached maxima after three hours. Furthermore, after three hours of translation reaction, the reaction solution was centrifuged for 10 minutes at 15,000 rpm so as to separate the soluble component, and when the ratio thereof was measured, the solubilization rate of both was on the order of 60%.

(3) Study of Glycosidase Inhibitors in the Wheat Embryo Extract

In analyzing the capability of the single-chain antisalmonella antibody synthesized in this manner to bind to the salmonella carbohydrate chain, it was found that the wheat embryo extract contained an enzyme that digests carbohydrate chains, and when the wheat embryo extract was used as described above, the resulting solution containing synthesized single-chain antibodies had an activity whereby the carbohydrate chains, which served as the antigens, were digested. Accordingly, an inhibitor of β-galactosidase, which is an enzyme that digests the salmonella carbohydrate chain, was added to the reaction solution in which the antigen binding experiment was performed. The β-galactosidase inhibitor was investigated by the following experiment.

Figure 2:
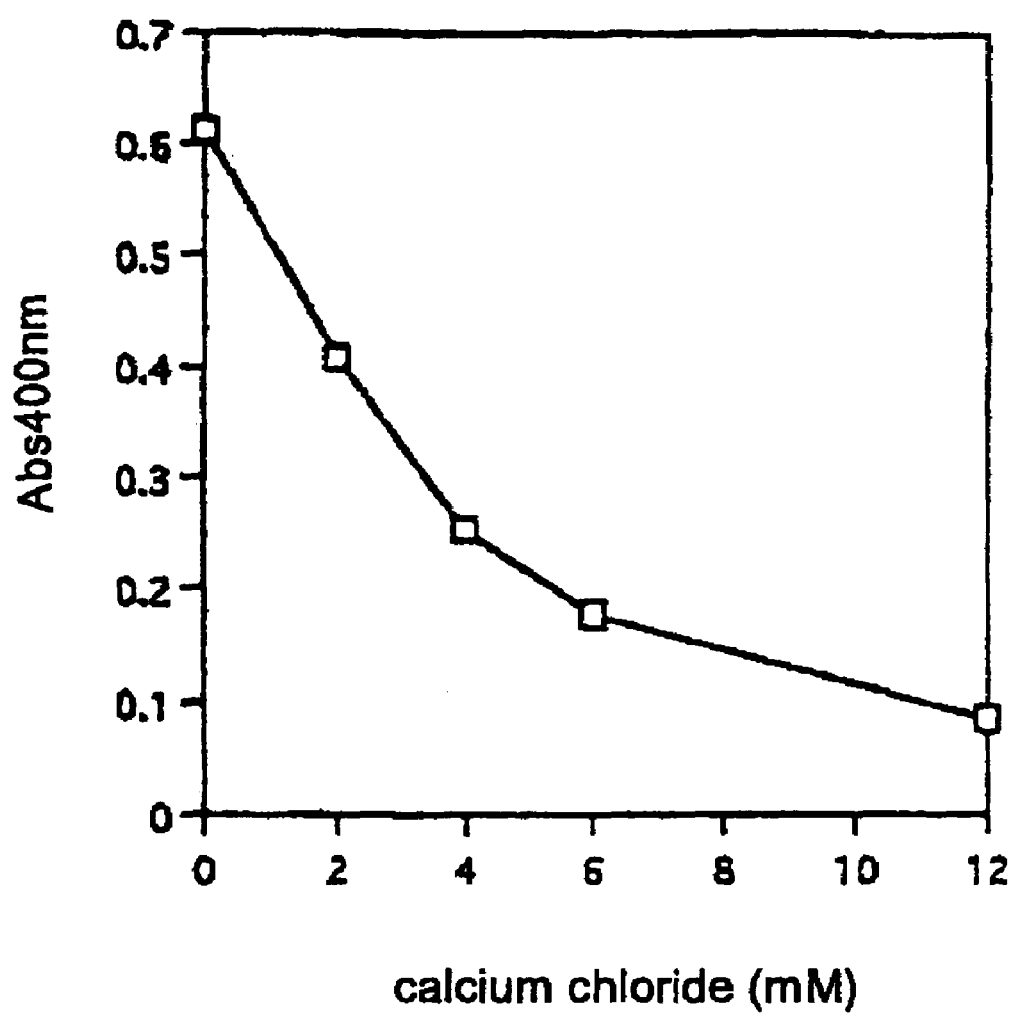
FIG. 2 is a graph showing calcium chloride inhibition of β-galactosidase activity in wheat embryo extract.

It is known that calcium chloride binds to the active site of β-galactosidase (Huber, R. E., et al., *Biochemistry*, 18, 4090-4095 (1979)). Here, the β-galactosidase activity in the wheat embryo extract was measured using p-nitrophenyl β-galactoside as a substrate. If calcium chloride is added at various concentrations (2 mM, 4 mM, 6 mM, and 12 mM) to 50 μl of the wheat embryo extract obtained in Experiment 1, as differs from the case where calcium chloride was not added (0 mM), precipitation occurs, which may be a result of increased salt concentration. This solution was centrifuged at 5,000 rpm for 10 minutes and the enzymatic activity of the supernatant produced was measured. The results are shown in FIG. 2. As can be understood from FIG. 2, the activity of the β-galactosidase contained in the supernatant is inhibited in a concentration dependent manner by calcium chloride. Thereupon, when 1.3 mM of EGTA was added to the supernatant and the precipitate, the enzymatic activity in the supernatant returned, but no specific change was seen in the enzymatic activity in the precipitate, which demonstrated that the β-galactosidase was present only in the supernatant and that the activity thereof was inhibited in a concentration dependent matter by adding calcium chloride.

Based on these results, 2.5 mM of calcium chloride was added beforehand when synthesizing the single-chain antisalmonella antibody used for analysis of binding to salmonella carbohydrate chains, and this was used for the translation reaction.

(4) Analysis of the Antigen Binding Capability of the Single-Chain Antisalmonella Antibody Synthesized Using the Weakly Reducing Synthesis Reaction Solution (4-1) Antigen Biotinylation In order to recover the antibody bound to the carbohydrate chain, which is the antigen, biotin was bound to the antigen. The method of preparing the biotinylated carbohydrate chain was based on a method described in the literature (Melkel, P., et al., *J. Immunol. Methods*, 132, 255-261 (1990)). Lipopolysaccharide (SIGMA) in the amount of 20 mg (2.8 μmol) was dissolved in 20 μl of 0.25 M aqueous sodium hydroxide and stirred for 1 hour at 56° C. After dialysis against distilled water, 200 mg (0.8 mmol) of sodium metaperfolate was added, and this was stirred in the dark for 5 minutes. Ethylene glycol in the amount of 1 ml was further added and this was stirred for 1 hour, whereafter it was dialyzed against distilled water and freeze-dried to produce an aldehydic salmonella carbohydrate chain powder.

This was dissolved in 3 ml of 0.2 M $MK_2HPO_4$—NaOH buffer solution (pH 8.0), and to 1.5 ml of this were added to 30 mg of 1,3-dl aminopropane (0.2 mmol) and 30 mg of $NaCNBH_3$ (0.5 mmol). After stirring for 1 hour, this was freeze-dried to produce an aminated salmonella carbohydrate chain powder. This was suspended in 600 μl of DMSO and 3.3 mg (0.1 mmol) of N-hydroxysuccinimidobiotin were added and stirring was continued gently overnight at room temperature. A further 1 ml of distilled water was added to this, whereafter gel filtration was performed using a Sephadex G-25 column.

Gel filtration was performed by loading 1.6 ml of a solution of the biotinated salmonella carbohydrate chain prepared as described above onto 120 ml of Sephadex G-25 gel (1.0×50 cm) which was equilibrated with distilled water, and eluting with 60 ml of distilled water. For each 2 ml fraction, neutral sugars were detected at 490 nm by the phenol-sulfuric acid method. After collecting the fraction in which the salmonella carbohydrate chain was found, this was freeze-dried and finally dissolved in 0.5 ml of 50 mM Tris-HCl buffer solution (pH 8.0) and used in the following analysis.

(4-2) Analysis of the Antigen Binding of the Single-Chain Antisalmonella Antibody To the cell-free protein synthesis reaction solution using wheat embryo extract described in Experiment 2(2) were added 2.5 mM of calcium chloride and also 0.5 μM of protein disulfide isomerase (PDI). The precipitate that formed by centrifugation was removed and the resulting solution was used for protein synthesis by adding the translation template described in Experiment 2(1). A quantity of 50 µl of the resulting cell-free protein synthesis reaction solution containing wild-type and mutant single-chain antisalmonella antibody was centrifuged for 10 minutes at 15,000 rpm to remove the insoluble proteins. To 28 µl of the supernatant were added 3 µl (280 µM) of the biotinated salmonella carbohydrate chain prepared in (4-1) and 14 µl of distilled water, this was incubated for 1 hour at 26° C. An amount of 16 µl of this solution were placed in an Eppendorf tube (500 µl) together with 25 µl of streptavidin-agarose gel (30 nmol/ml gel; SIGMA) and mixed gently at room temperature.

Following the reaction, the gel was precipitated using a micro-centrifuge whereafter, the supernatant was aspirated and in place of this 25 µl of 50 mM Tris-HCl buffer solution (pH 8.0) were added. Operations were repeated eight times wherein this was mixed for 10 minutes in the same manner, the gel was precipitated and the supernatant was suctioned. Next, 25 µl of 0.15M NaCl/50 mM Tris-HCl buffer solution (pH 8.0) were added. Operations were repeated four times wherein this was mixed for 10 minutes in the same manner, the gel was precipitated and the supernatant was suctioned. Next, an equal volume of 50 mM Tris-HCl buffer solution (pH 8.0) containing 4% SDS was added and mixed for 30 minutes. This operation was also repeated four times. Each of the supernatant components were TCA precipitated and the $^{14}$C counts were measured. The results are shown in FIG. 3.

Figure 3:
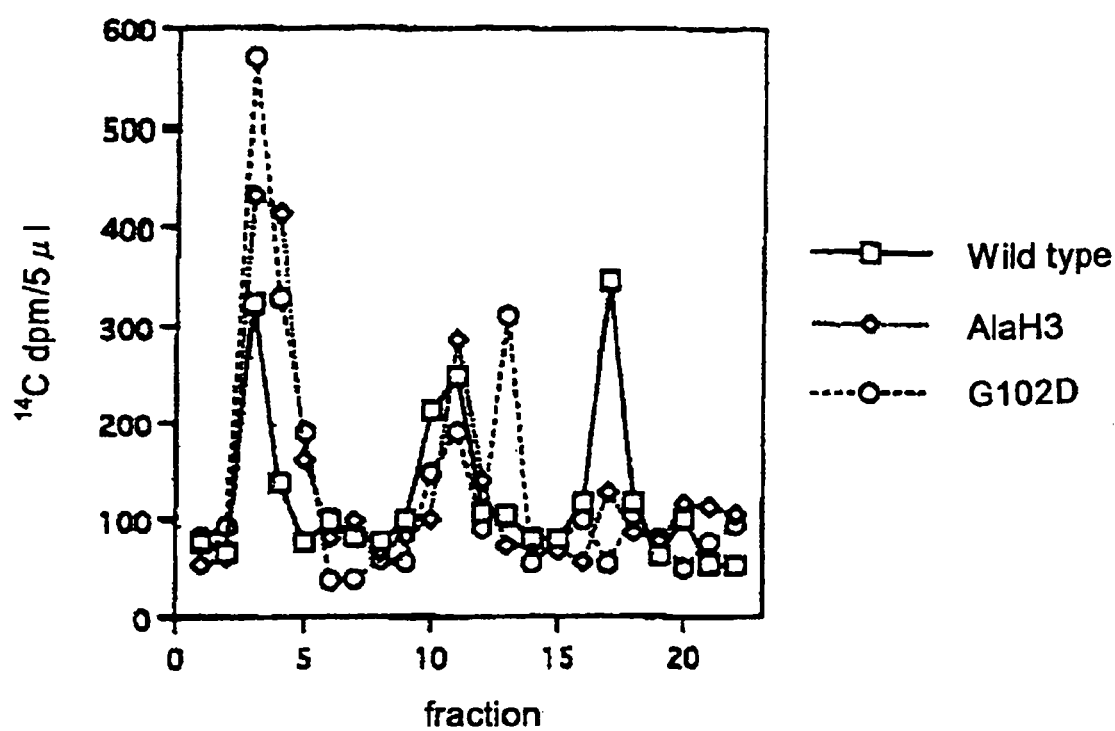
FIG. 3 is a graph showing the antigen binding capability of a single-chain antisalmonella antibody synthesized using a weakly reducing synthesis reaction solution.

In FIG. 3, the horizontal axis indicates the number assigned to the supernatant obtained as described above. Numbers 1 to 8 are the fractions eluted with 50 mM Tris-HCl buffer solution (pH 8.0); numbers 9 to 13 are the fractions eluted with 0.15 M NaCl/50 mM Tris-HCl buffer solution (pH 8.0); and numbers 14 to 22 are the fractions eluted with 50 mM Tris-HCl buffer solution (pH 8.0) containing 4% SDS. The antibody which bound specifically to the biotinated salmonella carbohydrate chain was eluted in fractions 14 to 22. As shown in FIG. 3, only the wild-type single-chain antisalmonella antibody bound specifically to the antigen. This shows that the antibody synthesized with the weakly reducing synthesis reaction solution, to which PDI was further added, possesses the original antibody function.

EXPERIMENT 3

Analysis of the Influence of the Concentration of the Reducing Agent and of PDI in the Synthesis Reaction Solution on the Formation of Intramolecular Disulfide Bonds within Synthesized Proteins Translation reactions using as a template the scfv-pEU, which contained DNA encoding the single-chain antisalmonella antibody obtained in Experiment 2(1), were performed at varying concentrations of DTT and PDI in the reaction solution, and the antigen binding capability was analyzed so as to analyze the influence on the intramolecular disulfide bond formation within the single-chain antisalmonella antibody protein synthesized. The translation reactions and the analysis of antigen binding capability were performed in the same way as described above in Experiment 2. For the cell-free protein synthesis reaction solution in these reactions, 12 µl of the wheat embryo extract prepared in Experiment 1 was used to prepare the following reaction solutions: (c) (redox potential: −14 mV, final DTT concentration 58 µM) wherein 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 4 nCi/µl of $^{14}$C Leu, and 7.5 µg of mRNA were added; (a) (redox potential: −230 mV) wherein DTT was further added to produce a final DTT concentration of 2 mM; (b) (redox potential: −237 mV) wherein DTT and PDI were added so that the final concentration of DDT was 2 mM and that of PDI was 0.5 µM; and (d) (redox potential: −21 mV) wherein PDI was added so that the final concentration of PDI was 0.5 µM. The results are shown in FIG. 4.

Figure 4:
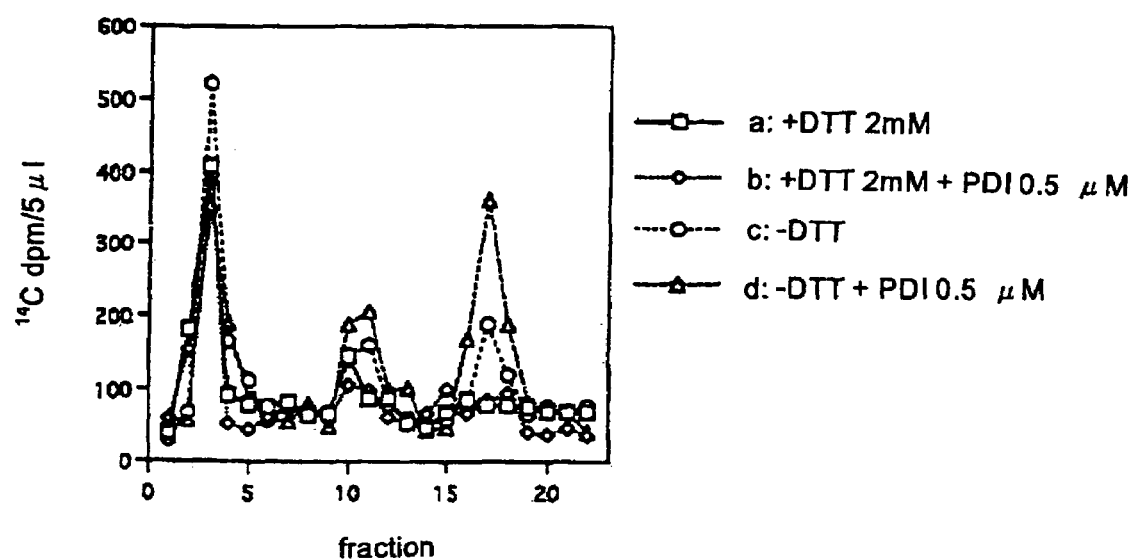
FIG. 4 is a graph showing the antigen binding capability of a single-chain antisalmonella antibody synthesized using cell-free protein synthesis reaction solutions which differed in terms of the reducing agent concentrations and the conditions under which protein disulfide isomerase (PDI) was added.

In FIG. 4, the horizontal axis indicates the number assigned to the supernatant eluted from the streptavidin-agarose. Numbers 1 to 8 are the fractions eluted with 50 mM Tris-HCl buffer solution (pH 8.0); numbers 9 to 13 are the fractions eluted with 0.15 M NaCl/50 mM Tris-HCl buffer solution (pH 8.0); and numbers 14 to 22 are the fractions eluted with 50 mM Tris-HCl buffer solution (pH 8.0) containing 4% SDS. The antibody which bound specifically to the biotinated salmonella carbohydrate chain was eluted in fractions 14 to 22. Furthermore, a to d indicate the compositions of the cell-free protein synthesis reaction solutions above.

As shown by FIG. 4, the single-chain antisalmonella antibody synthesized by translation using the weakly reducing synthesis reaction solution to which PDI had been added bound to the antigen at the highest rate while there was almost no antigen binding activity when the highly reducing synthesis reaction solution was used. Furthermore, with the weakly reducing synthesis reaction solution, the effect of adding PDI was pronounced.

Figure 5:
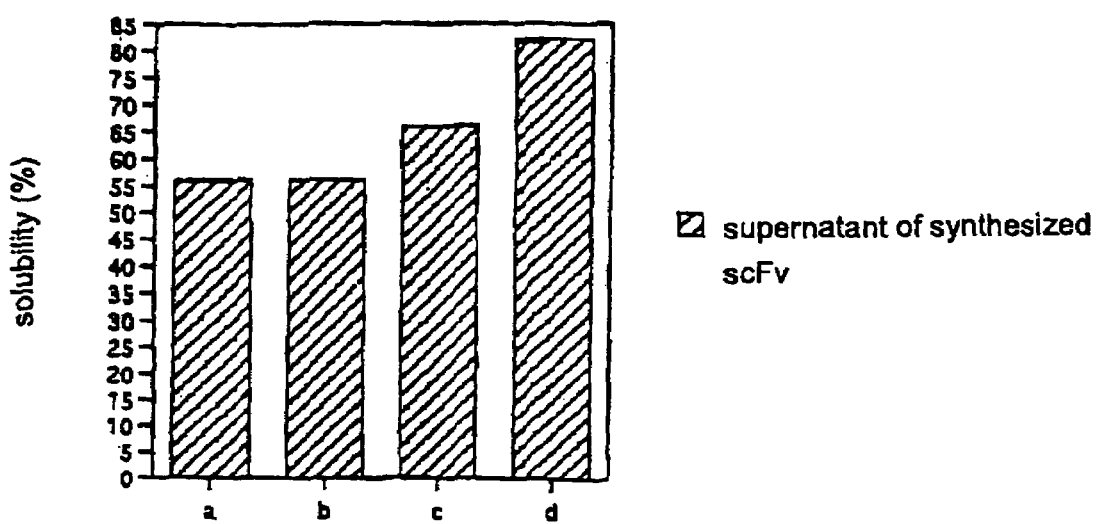
FIG. 5 is a graph showing the solubilization rate of single-chain antisalmonella antibodies synthesized using cell-free protein synthesis reaction solutions which differed in terms of the reducing agent concentrations and the conditions under which PDI was added.

The various synthesis reaction solutions described above were centrifuged for 10 minutes at 15,000 rpm to separate the solubilized component and the ratio thereof was measured. The results are shown in FIG. 5. Furthermore, a to d indicate the compositions of the synthesis reaction solutions above, while the vertical axis indicates the solubilization rates of the proteins produced.

Fifty percent of the protein synthesized with a cell-free protein synthesis reaction solution containing a high concentration of DTT was soluble (solubilization rate: 50%) but when the DTT concentration was low, this ratio increased to no less than 65% (solubilization rate: no less than 65%) and by adding PDI this reached approximately 80% (solubilization rate: 80%).

These results show that the formation of a disulfide bond within the protein molecule so as to synthesize protein possessing the original function of the protein in a cell-free protein synthesis reaction system can be determined by using the increase in the protein solubilization rate in the resulting cell-free protein synthesis reaction solution, brought about by adding PDI, as an indicator.

EXAMPLE 4

Analysis of the Influence of the Concentration of the DTT in the Cell-Free Protein Synthesis Reaction Solution on the Formation of Intramolecular Disulfide Bonds within Synthesized Proteins Translation reactions using as a template the scfv-pEU, which contained DNA encoding the single-chain antisalmonella antibody obtained in example 2(1) were performed at varying concentrations of DTT in the reaction solution, and the solubilization rate in the cell-free protein synthesis reaction solution was analyzed in order to analyze the influence on the intramolecular disulfide bond formation in the single-chain antisalmonella antibody synthesized. The translation reaction and the analysis of the protein solubilization rate in the cell-free protein synthesis reaction solution were performed in the same way as described in Experiments 2 and 3. For the cell-free protein synthesis reaction solution in these reactions, 12 µl of the wheat embryo extract prepared in Experiment 1 was used to prepare a reaction solution (redox potential: −14 mV, final DTT concentration 58 µM) wherein 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 2 nCi/µl of $^{14}$C-Leu, and 7.5 µg of mRNA were added, and to prepare reaction solutions wherein DTT was further added in amounts that produced final DTT concentrations of 50 µM, 100 µM (with redox potentials of −52 mV. −81 mV, respectively). Furthermore, in order to analyze the effect of adding PDI on the protein solubilization rate in the cell-free protein synthesis reaction solutions, synthesis was performed using reaction solutions having the same compositions, to which 0.5 µM of PDI had been added. The results are shown in FIG. 6.

Figure 6:
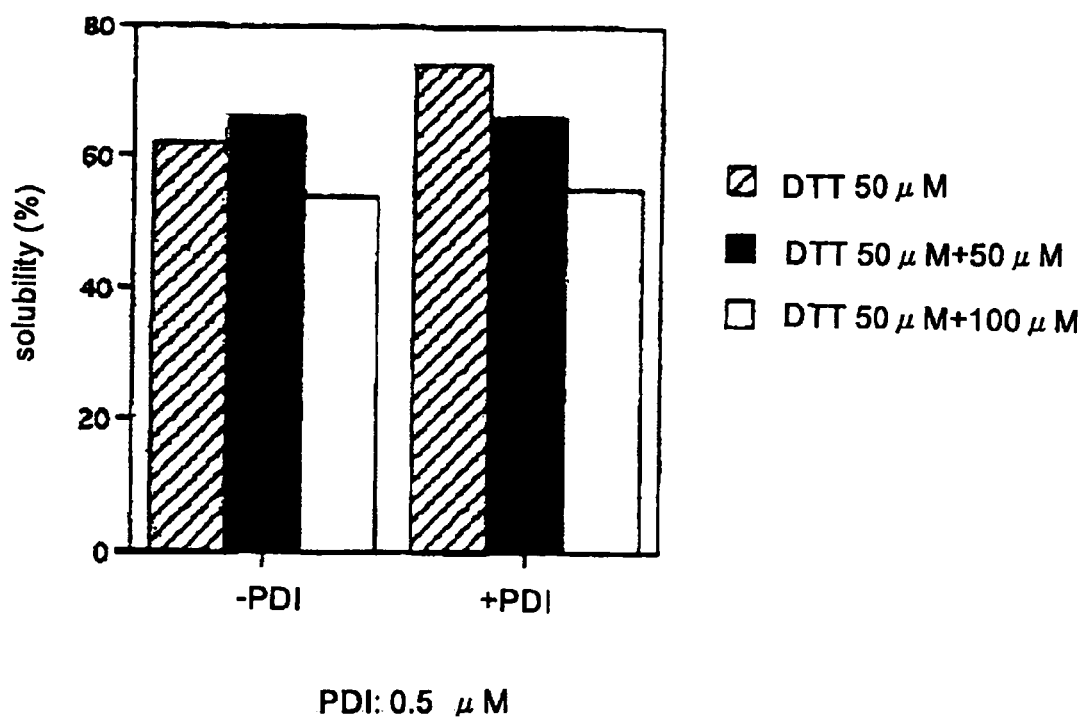
FIG. 6 is a graph showing the solubilization rate of single-chain antisalmonella antibodies synthesized using cell-free protein synthesis reaction solutions which differed in terms of DTT concentrations and the conditions under which PDI was added.

In FIG. 6, the left-hand column (−PDI) shows the results for the reactions in which PDI was not present, and the right hand column (+PDI) shows the results for the reactions in which PDI was present. FIG. 6 shows that when DTT was present in the cell-free protein synthesis reaction solution at concentrations of greater than 50 µM, the effect of increasing the solubilization rate as a result of PDI added was not observed.

EXPERIMENT 5

Analysis of the Influence of the Concentration of DTT in the Cell-Free Protein Synthesis Reaction Solution on the Amount of Protein Synthesized Based on Experiment 4, it was determined that the formation of at least one intramolecular disulfide bond in the protein necessitated a DTT concentration of no greater than 50 µM in the cell-free protein synthesis reaction solution of the cell-free protein synthesis system. However, as DTT is known to be necessary to this synthesis system, analysis was made of the influence of this concentration on the amount of protein synthesized.

The translation template, the translation reaction, and measurement of the amount of protein synthesized were all performed according to the same methods as described above in Experiments 2(1) and 2(2). The scfv-pEU was used as the template. Furthermore, a reaction solution wherein 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 2 nCi/µl of $^{14}$C-Leu, and 7.5 µg of mRNA was added to the 12 µl of the wheat embryo extract prepared in Experiment 1 (redox potential: −14 mV, final concentration of DTT: 58 µM), and reaction solutions wherein DTT was further added to produce final concentrations of 180 µM, 360 µM, 600 µM, 840 µM, 1.2 mM, and 3 mM (redox potentials: −95 mV, −130 mV, −170 mV, −180 mV, −200 mV, and −230 mV, respectively) were used for the cell-free protein synthesis reaction solution. Furthermore, reaction solutions were used wherein 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 2 nCi/µl of $^{14}$C-Leu, and 7.5 µg of mRNA were added to 12 µl of a solution prepared by adjusting the concentration of DTT contained in the wheat embryo extract prepared in Experiment 1 to 15 µM by means of dialysis and 12 µl of a solution having a DTT concentration of 30 µM, which was not subject to dialysis (having redox potentials of +20 mV and −9 mV respectively). The results are shown in FIG. 7.

Figure 7:
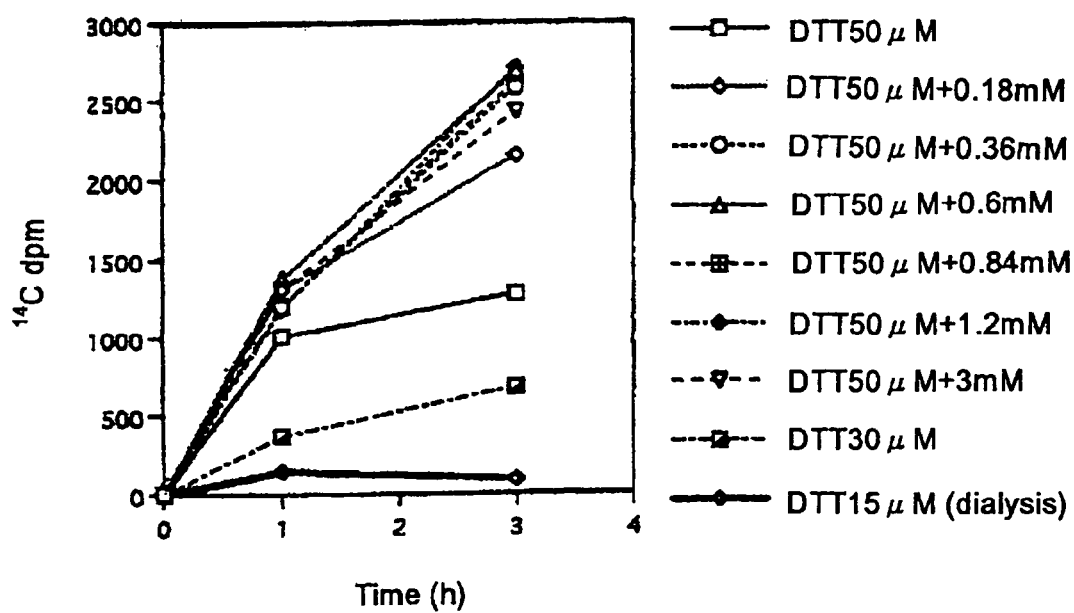
FIG. 7 is a graph showing the amount of single-chain antisalmonella antibodies synthesized using cell-free protein synthesis reaction solutions which differed in terms of DTT concentration addition conditions.

FIG. 7 shows that the most protein was synthesized using a cell-free protein synthesis reaction solution having a DTT concentration on the order of 1.2 mM. With a cell-free protein synthesis reaction solution having a DTT concentration of 50 µM, which is the most suited to the formation of intramolecular disulfide bonds, the amount of proteins synthesized was approximately 50% of this amount. Furthermore, at a DTT concentration of 30 µM, this was approximately 40%, and protein synthesis did not occur at a DTT concentration of 15 µM.

EXPERIMENT 6

Analysis of the Influence of the Concentration of 2-Mercaptoethanol in the Cell-Free Protein Synthesis Reaction Solution on the Formation of Intramolecular Disulfide Bonds in Proteins Translation reactions using as a template the scfv-pEU, which contained DNA encoding the single-chain antisalmonella antibody obtained in Experiment 2(1) were performed at varying concentrations of 2-mercaptoethanol in the reaction solution, and the solubilization rate of the cell-free protein synthesis reaction solution was analyzed, in order to analyze the influence on intramolecular disulfide bond formation in the single-chain antisalmonella antibody protein synthesized. The translation reaction and the analysis of the solubilization rate of protein in the cell-free protein synthesis reaction solution were performed in the same way as described in Experiments 2 and 3. For the cell-free protein synthesis reaction solution in these reactions, 12 µl of the wheat embryo extract prepared in Experiment 1 was used to prepare a reaction solution containing 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 2 nCi/µl of $^{14}$C-Leu, and 7.5 µg of mRNA, and 2-mercaptoethanol was added in amounts producing final 2-mercaptoethanol concentrations of 0.2 mM, 0.4 mM, 0.96 mM, and 9.6 mM (with redox potentials of −35 mV. −63 mV, −168 mV, and −207 mV, respectively). Furthermore, in order to analyze the effect of PDI on the protein solubilization rate in the various cell-free protein synthesis reaction solutions, synthesis was performed using reaction solutions having the same compositions, to which 0.5 µM of PDI had been added. The results are shown in FIG. 8.

Figure 8:
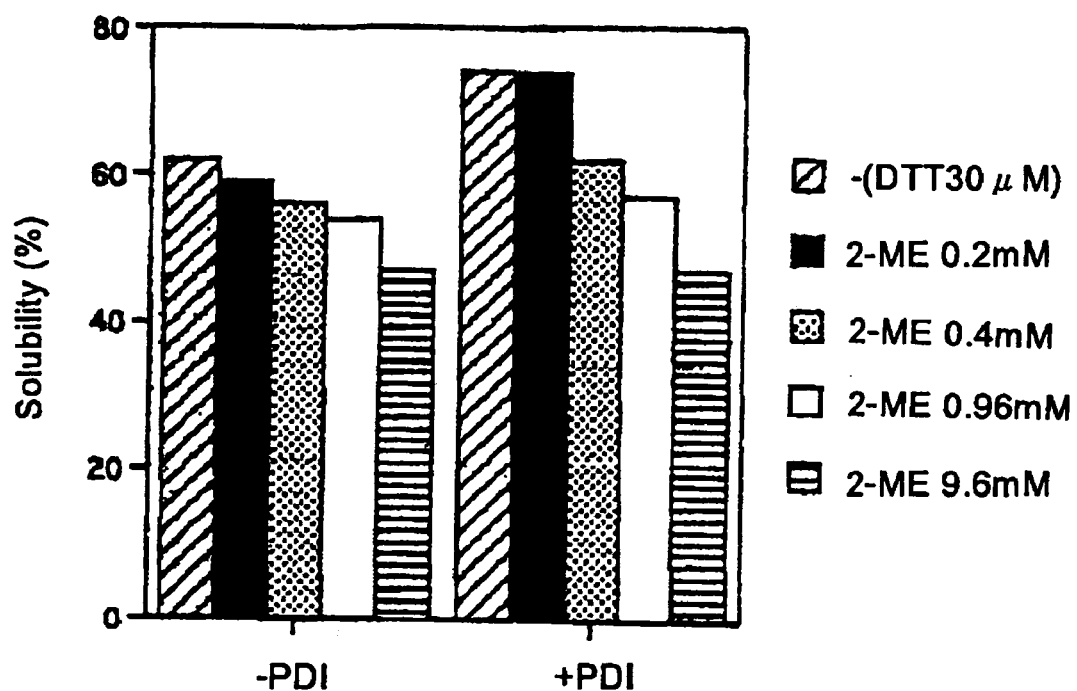
FIG. 8 is a graph showing the solubilization rate of single-chain antisalmonella antibodies synthesized using cell-free protein synthesis reaction solutions which differed in terms of mercaptoethanol concentrations and the conditions under which PDI was added.

In FIG. 8, the left-hand column (−PDI) shows the results for the reactions in which PDI was not present, and the right-hand column (+PDI) shows the results for the reactions in which PDI was present. Note that FIG. 8 shows the DTT concentration of 30 µM in Experiment 5 as a reference. FIG. 8 shows that, when mercaptoethanol is comprised at a concentration of greater than 0.2 mM in the cell-free protein synthesis reaction solution, the effect of increasing the solubilization rate as a result of PDI is not observed.

Furthermore, when the amounts of protein synthesized by the cell-free protein synthesis reaction solutions were measured by the same method as in Experiment 5, it was determined that, even when using a cell-free protein synthesis reaction solution to which mercaptoethanol had been added in an amount producing a final concentration of 0.2 mM, the drop in the amount of protein synthesized held steady at approximately 10%.

EXPERIMENT 7

Analysis of the Influence of the Concentration of Glutathione/oxidized Glutathione in the Cell-Free Protein Synthesis Reaction Solution on the Formation of Intramolecular Disulfide Bonds in Synthesized Proteins Translation reactions using as a template the scfv-pEU, which contained DNA encoding the single-chain antisalmonella antibody obtained in example 2(1) were performed at varying concentrations of glutathione/oxidized glutathione in the reaction solution, and the solubilization rate in the cell-free protein synthesis reaction solution was analyzed, in order to analyze the influence on the intramolecular disulfide bond formation in the single-chain antisalmonella antibody protein synthesized. The translation reaction and the analysis of the protein solubilization rate in the cell-free protein synthesis reaction solution were performed in the same way as described in Experiments 2 and 3.

For the cell-free protein synthesis reaction solution in these reactions, 12 µl of the wheat embryo extract prepared in Experiment 1 was used to prepare a reaction solution containing 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 2 nCi/µl of $^{14}$C-Leu, and 7.5 µg of mRNA (redox potential: −14 mV, final DTT concentration 58 µM), and glutathione/oxidized glutathione were further added in amounts producing final glutathione/oxidized glutathione concentrations of 50 µM/5 µM, 200 µM/20 µM (with redox potentials of −3 mV and −6 mV, respectively). Furthermore, in order to analyze the effect of adding PDI on the protein solubilization rate in the cell-free protein synthesis reaction solutions, synthesis was performed using reaction solutions with the same compositions to which 0.5 µM of PDI had been added. The results are shown in FIG. 9.

Figure 9:
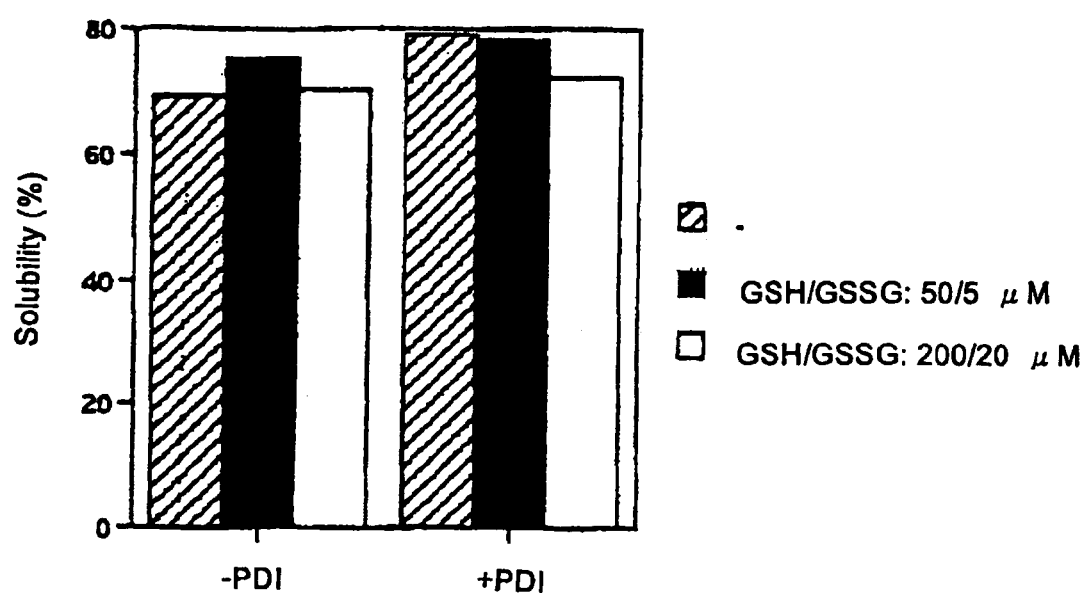
FIG. 9 is a graph showing the solubilization rate of single-chain antisalmonella antibodies synthesized using cell-free protein synthesis reaction solutions which differed in terms of glutathione/oxidized glutathione concentrations and the conditions under which PDI was added.

In FIG. 9, the left-hand column (−PDI) shows the results for the reaction in which PDI was not present, and the right-hand column (+PDI) shows the results for the reaction in which PDI was present. FIG. 9 shows that if glutathione/oxidized glutathione are comprised at concentrations of greater than 50 µM/5 µM in the cell-free protein synthesis reaction solution, the effect of increasing the solubilization rate as a result of PDI added is not observed.

Furthermore, when the amounts of proteins synthesized by the cell-free protein synthesis reaction solutions were measured by the same method as in Experiment 5, it was determined that, even when using a cell-free protein synthesis reaction solution to which glutathione/oxidized glutathione had been added in amounts producing final concentrations of 50 µM/5 µM, the drop in the amount of protein synthesized held steady at approximately 10%.

EXPERIMENT 8

Study of the Times at Which PDI is Added in the Translation Reaction Using the Weakly Reducing Synthesis Reaction Solution Translation reactions using as a template the scfv-pEU, which contained DNA encoding the single-chain antisalmonella antibody obtained in Experiment 2(1) were performed with the times at which the PDI was added to the reaction solution varied, and the antigen binding capability was analyed, in order to analyze the influence on the intramolecular disulfide bond formation within the single-chain antisalmonella antibody protein synthesized. The translation reaction and the analysis of the antigen binding capability were performed in the same way as described above in Experiment 2. For the cell-free protein synthesis reaction solution in these reactions, 12 µl of the wheat embryo extract prepared in Experiment 1 was used to prepare a reaction solution containing 1.2 mM of ATP, 0.25 mM of GTP, 15 mM of creatine phosphate, 0.4 mM of spermidine, 29 mM of HEPES-KOH (pH 7.6), 95 mM of potassium acetate, 2.7 mM of magnesium acetate, 0.23 mM of L-amino acids, 0.58 U/µl of RNase inhibitor (Promega), 4 nCi/µl of $^{14}$C-Leu, and 7.5 µg of mRNA (redox potential: −14 mV, final DTT concentration 58 µM). Furthermore, cases were studied wherein the same amount of PDI was added after two hours of translation reaction, and wherein this was not added. The results are shown in FIG. 10.

Figure 10:
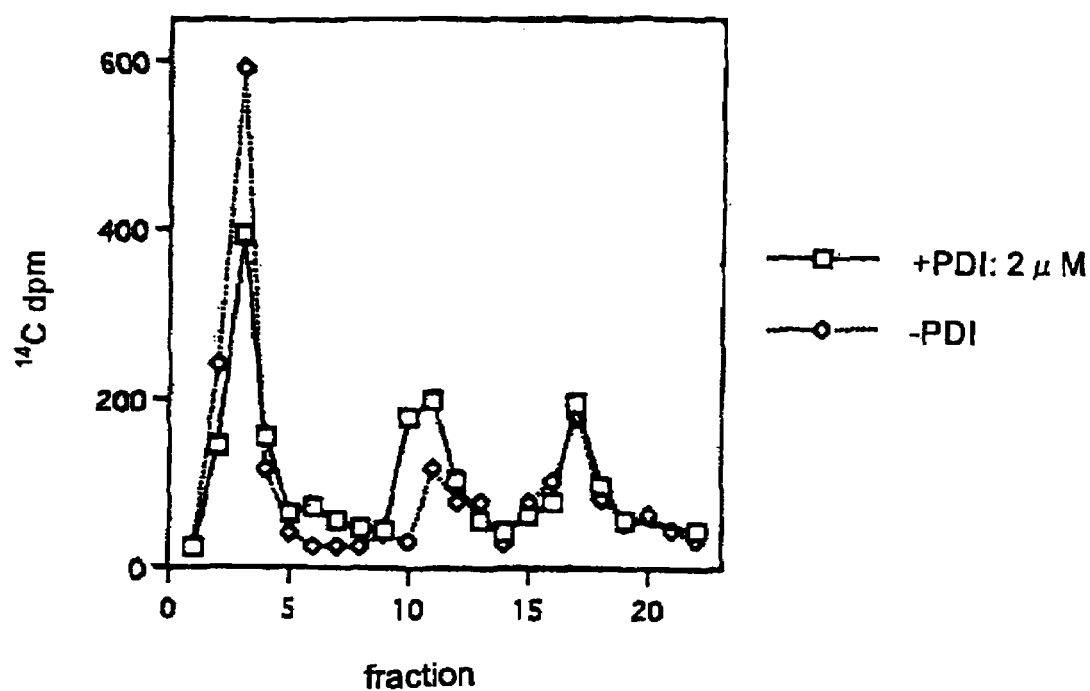
FIG. 10 is a graph showing the antigen binding capability of a single-chain antisalmonella antibody synthesized using a weakly reducing synthesis reaction solution, to which PDI was added at different times.

In FIG. 10, the horizontal axis indicates the number assigned to the supernatant eluted from the streptavidin-agarose. Numbers 1 to 8 are the fractions eluted with 50 mM Tris-HCl buffer solution (pH 8.0); numbers 9 to 13 are the fractions eluted with 0.15 M NaCl/50 mM Tris-HCl buffer solution (pH 8.0); and numbers 14 to 22 are the fractions eluted with 50 mM Tris-HCl buffer solution (pH 8.0) containing 4% SDS. The antibody which bound specifically to the biotinated salmonella carbohydrate chain was eluted in fractions 14 to 22. Furthermore, the +PDI indicates the results of adding PDI after two hours of translation reaction and the −PDI indicates the results of using a cell-free protein synthesis reaction solution to which PDI was not added.

As can be seen from FIG. 10, when PDI is added after the translation reaction has gone forward, no difference is observed in the amount of single-chain antisalmonella antibody binding to the antigen synthesized, as compared to that where PDI is not added. This shows that PDI does not induce the disulfide bond after completion of the translation reaction but rather catalyzes a disulfide bond exchange reaction while the translation reaction is progressing.

Possibilities for Industrial Use

By virtue of the present invention, using a cell-free protein synthesis system, it is possible to synthesize proteins in which at least one intramolecular disulfide bond is formed, which could not heretofore be efficiently synthesized. Antibodies are one example of proteins having at least one intramolecular disulfide bond. Antibodies have strong antigen binding capability and high antigen specificity. Consequently, in cases where it is necessary to immunize animal cells with a specific artificial antigen, a definitive problem arose in that products lethal to the organism were eliminated. Cell-free protein synthesis systems do not present this concern and therefore, by means of the method of the present invention, medicinal antibodies can be supplied for an almost limitless repertory of antigens. Furthermore, the antibodies synthesized in the present experiments for carbohydrate chain antigens can be supplied to means which are extremely useful in developing technology for simulation of carbohydrate chain/protein interaction.

The present application is based on Japanese Patent Application 2002-053161, the entire contents of which are incorporated herein.

The invention claimed is:

1. A cell-free protein synthesis reaction solution comprising dithiothrcitol of a concentration from 20 μM to 70 μM, wherein said cell free protein synthesis reaction solution allows for protein synthesis.

2. A cell-free protein synthesis reaction solution comprising 2-mercaptoethanol of a concentration from 0.1 mM to 0.2 mM wherein said cell free protein synthesis reaction solution allows for protein synthesis.

3. A cell-free protein synthesis reaction solution prepared from wheat embryo comprising glutathione of a concentration from 30 μM to 50 μM that is added, and/or oxidized glutathione of a concentration from 1 μM to 5 μM that is added wherein said cell free protein synthesis reaction solution allows for protein synthesis.

* * * * *